United States Patent [19]

Trenkle et al.

[11] 4,217,252
[45] Aug. 12, 1980

[54] PERFUME COMPOSITIONS CONTAINING 1-ACYL-2,6,6-TRIMETHYLCYCLOHEXENE DERIVATIVES

[75] Inventors: Robert W. Trenkle, Bricktown; Braja D. Mookherjee, Holmdel; Robin Kasper, Eatontown; Manfred H. Vock, Locust; Joaquin Vinals, Red Bank, all of N.J.; Jacob Kiwala, Brooklyn, N.Y.; Frederick L. Schmitt, Holmdel, N.J.

[73] Assignee: International Flavors & Fragrances Inc., New York, N.Y.

[21] Appl. No.: 39,193

[22] Filed: May 15, 1979

Related U.S. Application Data

[62] Division of Ser. No. 965,418, Dec. 1, 1978, Pat. No. 4,172,850.

[51] Int. Cl.² .............................................. C11B 9/00
[52] U.S. Cl. ............................... 252/522 R; 252/108; 252/173; 252/174.11; 424/52; 424/176; 424/184; 424/201; 426/538; 426/589; 426/597; 426/650; 560/125; 560/170; 568/826; 568/378; 568/345; 568/347; 568/350; 131/17 R
[58] Field of Search ........................................ 252/522

[56] References Cited

U.S. PATENT DOCUMENTS

| | | | |
|---|---|---|---|
| 2,853,520 | 9/1958 | Newman | 260/586 R |
| 3,956,392 | 5/1976 | de Haan et al. | 260/586 P |
| 4,081,479 | 3/1978 | Hall et al. | 252/522 R |

OTHER PUBLICATIONS

Fieser et al., Reagents for Org. Chem., vol. 1, pp. 566, 567, 1776, 1777, John Wiley & Sons, 1974.
Chanley et al., J. Amer. Chem. Soc., vol. 77, p. 6056, 1955.
Cookson et al., Chem. Ab. 80:27395w, 1974.
Bucchi, Chem. Ab. 78:110669t, 1973.
Schulte-Elte et al., Chem. Ab. 79:42041a, 1973.

*Primary Examiner*—Veronica O'Keefe
*Attorney, Agent, or Firm*—Arthur L. Liberman

[57] ABSTRACT

Described is a process for augmenting or enhancing the aroma of a perfume composition as well as perfume and cologne compositions containing a mixture consisting essentially of compounds having the structures:

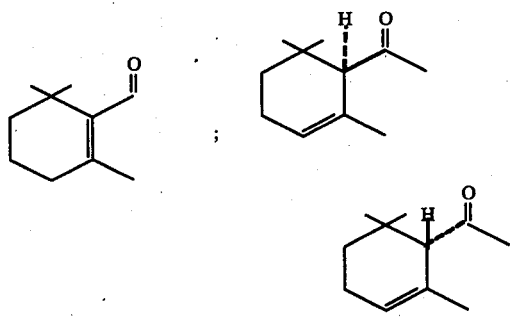

and wherein the mixture contains 30% of the compounds having the structures;

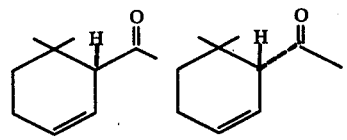

and 60% of the compound having the structure:

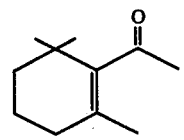

3 Claims, 9 Drawing Figures

GLC PROFILE FOR EXAMPLE I

NMR SPECTRUM FOR EXAMPLE I, PEAK 3.

IR SPECTRUM FOR EXAMPLE I, PEAK 2.

IR SPECTRUM FOR EXAMPLE I, PEAK 3.

MASS SPECTRUM FOR EXAMPLE II, PEAK 2.

MASS SPECTRUM FOR EXAMPLE II, PEAK 3.

IR SPECTRUM FOR EXAMPLE II, FRACTION 3.

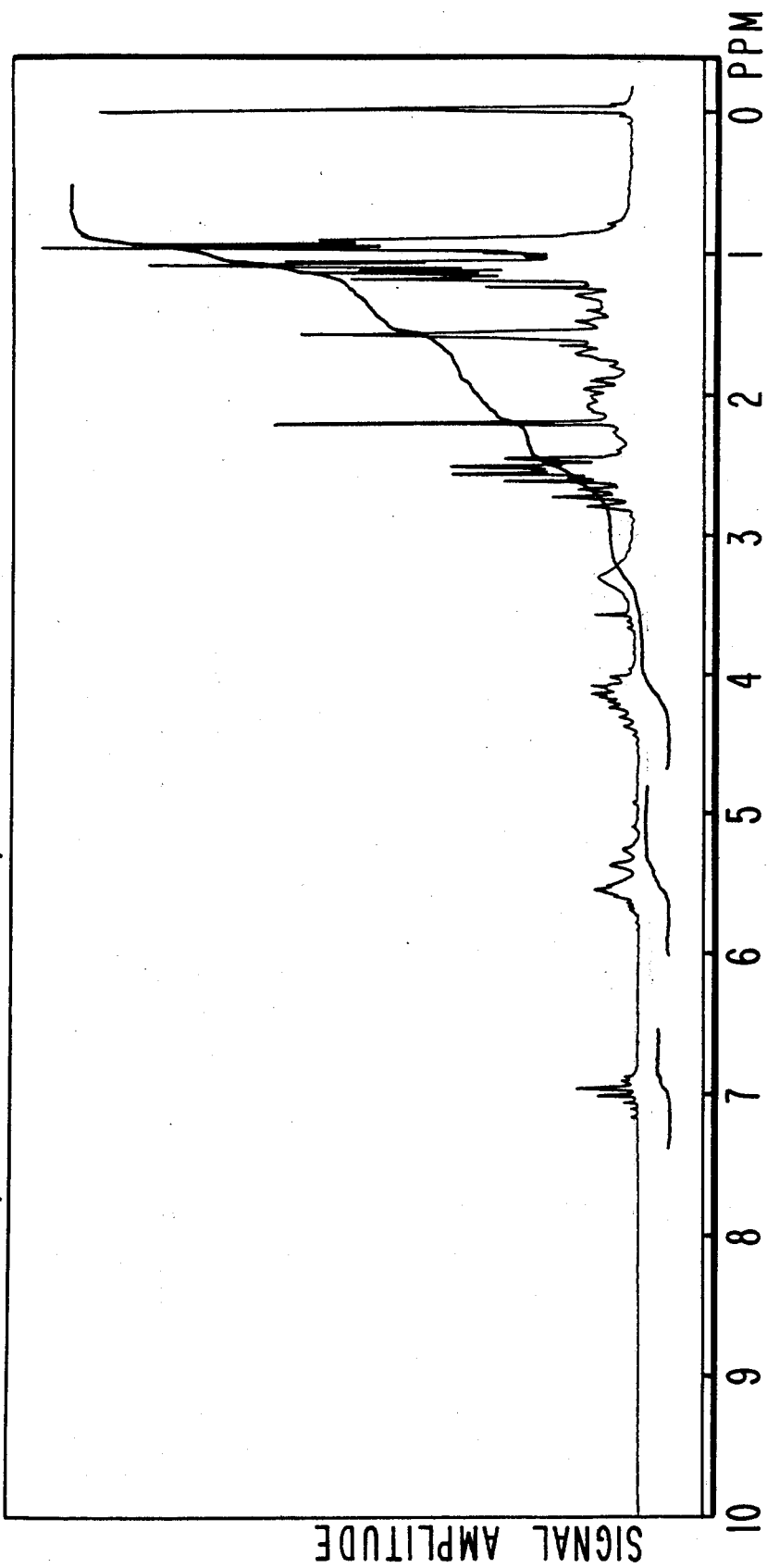
FIG. 9 NMR SPECTRUM, FOR EXAMPLE II, FRACTION 3.

PERFUME COMPOSITIONS CONTAINING 1-ACYL-2,6,6-TRIMETHYLCYCLOHEXENE DERIVATIVES

This is a divisional of application Ser. No. 965,418, filed Dec. 1, 1978, now U.S. Pat. No. 4,172,850.

BACKGROUND OF THE INVENTION

The present invention provides the compounds having the generic structure:

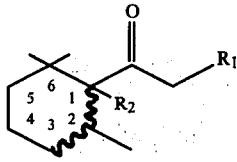

wherein $R_1$ is hydrogen or ethylidene having the structure:

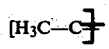

and $R_2$ is hydrogen or no group; wherein one of the wavy lines is a carbon-carbon double bond and the other of the wavy lines is a carbon-carbon single bond; with the proviso that when the $\Delta^{2,3}$ bond is a carbon-carbon double bond, $R_2$ is hydrogen and $R_2$ and the moiety:

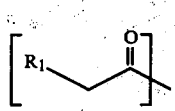

are so juxtaposed that the molecule having the structure:

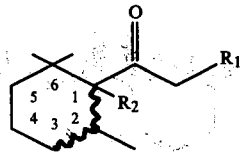

exists in two different isomeric forms; a "+" and a "−" form. Such compounds are provided by a novel process of our invention described hereinafter which gives rise to novel intermediates including the compounds having the generic structure:

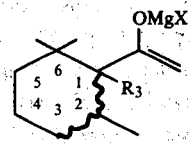

wherein X is chloro, bromo or iodo, $R_3$ is hydrogen or no group; wherein one of the wavy lines is a carbon-carbon double bond and the other of the wavy lines is a carbon-carbon single bond; with the proviso that when the $\Delta^{2,3}$ bond is a carbon-carbon double bond, then $R_3$ is hydrogen and $R_3$ and the moiety:

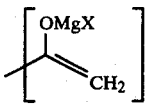

are so juxtaposed that the molecule having the structure:

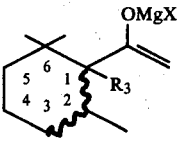

exists in two different forms; a "+" and a "−" form.

Compounds produced using the processes of our invention including a number of the intermediates produced are useful for their organoleptic properties in perfumes, perfumed articles, foodstuffs, foodstuff flavoring compositions, chewing gums, toothpastes, medicinal products, tobaccos, tobacco flavoring compositions, substitute tobaccos and substitute tobacco flavoring compositions.

In the perfumery art, there is a considerable need for substituents having sweet, floral, fruity, rose-like, minty/camphoraceous aromas with floral, hay-like, musty backgrounds and tobacco nuances. Specifically described herein are materials having such organoleptic profiles but which do not discolor with age. Such fragrance materials have a wide utilization in the presence of these perfume compounds. A limited amount of such materials that give rise to these properties is available from natural sources but the natural materials are subject to wide variations in quality, or are expensive, and/or often in critically short supply. This particularly holds true for the use of alpha damascone, beta damascone and mixtures of alpha damascone and beta damascone.

In addition, there is a continuing search for food flavor compositions which can vary, fortify, modify, enhance, augment or otherwise improve the flavor and/or aroma of foodstuffs, medicinal products, toothpastes, and chewing gums. To be satisfactory, such compositions should be stable, non-toxic and blendable with other ingredients to provide their own unique flavor and aroma nuances without detracting from the co-ingredients of the formulations in which they are used. Preferably, such compositions should be naturally occurring or present in natural foodstuffs so that their ingestible safety can be readily recognized. These materials should be capable of being synthesized in a simple and economical manner. The need for safe flavors in the mint, lemon and tropical fruit flavor area is well known particularly in the ice cream and yogurt flavor areas. More specifically, there is a need for the development of non-toxic materials which can replace natural materials not readily available, having herbaceous, earthy, patchouli-like, damascenone-like, lemony and minty aroma and flavor characteristics.

In tobacco flavoring art (pertaining to tobaccos and substitute tobaccos) there is a considerable need for substituents having musty-floral, slightly sweet, fruity and damascenone-like aromas and tastes in tobacco prior to smoking and sweet, Virginia tobacco-like notes on smoking in both the main stream and the side stream.

Specifically described herein are materials having such an organoleptic profile but which do not discolor with age.

The instant invention provides the foregoing, which the prior art has heretofore fails to provide. Furthermore, nothing in the prior art shows the unexpected, unobvious and advantageous value of the compounds having the structures:

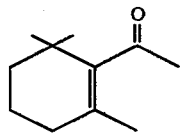 ; 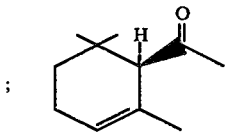

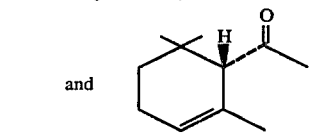

for their organoleptic properties.

The compounds having the structures:

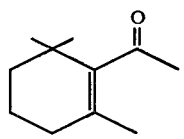 ; 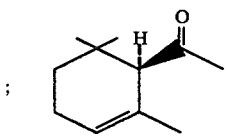

and

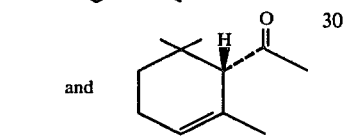

are disclosed in the prior art at:
Chem. Abstracts, Vol. 78, No. 110669t (Abstracts of J. Org. Chem. 1973, 38 [5], 894–6);
Chem. Abstracts, Vol. 80, No. 27395w (Abstracts of J. Chem. Soc., Chem. Communications 1973 [19], 7842; and at
Chem. Abstracts, Vol. 79, No. 42041a (Abstract of German Offlegungschrift 2,244,680). German Offlegungschrift 2,244,680 includes a genus which could read on the compound having the structure:

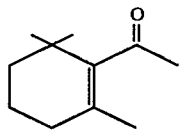

but no specific disclosure thereof is made in said German Offlegungschrift.

In addition, the preparations of these compounds have been carried out in a rather complex manner as is shown in:
Chem. Abstracts 54:345f (U.S. Pat. No. 2,853,520);
Chem. Abstracts, Vol. 50, 8540h (Abstract of Chanley, et al, J. Am. Chem. Soc. 77, 6056–7 [1955]);
Chem. Abstracts 50:15442b (Abstract of Landor, J. Chem. Soc., 1956, 1015–1019);
Chem. Abstracts, Vol. 48, 13644i (Abstract of Newman, J. Am. Chem. Soc., 75, 4740–2 [1953]); and
Chem. Abstracts, Vol. 47:1098h (Abstract of Henbest, et al, J. Am. Chem. Soc., 1952, 1150–4)

Nothing in the prior art, however, discloses a process whereby a compound having the structure:

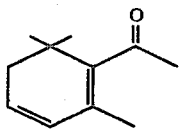

can be hydrogenated using a Lindlar catalyst to form compounds having the structures:

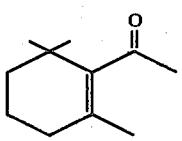 ; 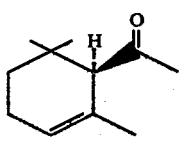

and

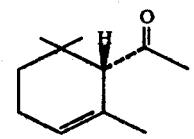

Another group of products produced as a result of using the processes of our invention are alpha-damascone and beta-damascones having the structures:

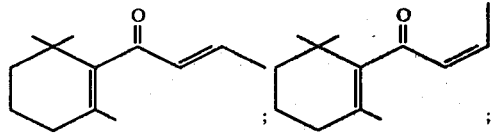

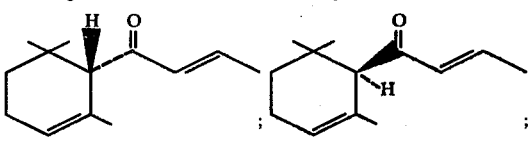

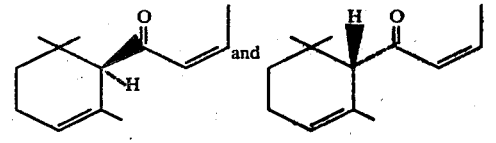

These compounds are shown to be useful for their organoleptic properties by Kovats at Chem. Abstracts, Vol. 74, page 76564k ("Cycloaliphatic Unsaturated Ketones for Use as Perfumes").

Mixtures, presumably predominantly cis,trans-Δ-damascone with minor amounts of trans, trans-Δ-damascone have been produced by Ayyar, Cookson and Kagi as set forth in J. Chem. Soc., Perkin Trans. 1, 1975 (17) 1727–36 [Title: "Synthesis of δ-Damascone[-trans-1-(2,6,6-Trimethylcyclohex-3-enyl)but-2-en-1-one] and β-Damascenone [trans-1-(2,6,6-Trimethylcyclohexa-1,3-dienyl)but-2-en-1-one]"]. The reaction sequence of the Ayyar synthesis of compositions presumed to be predominantly cis, trans-Δ-damascone with minor amounts of trans, trans-Δ-damascone is as follows:

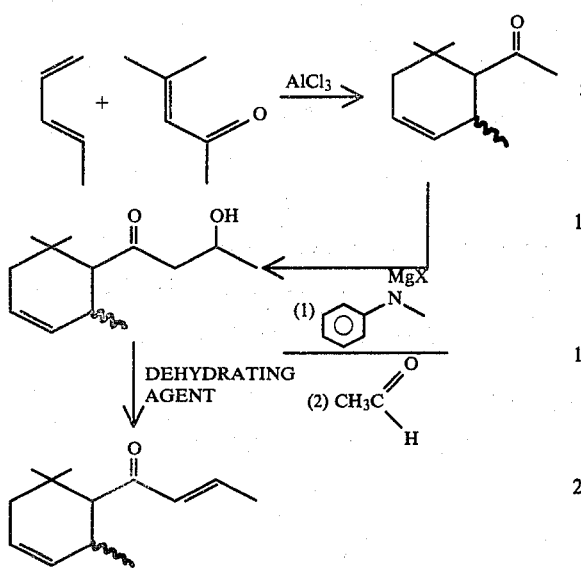

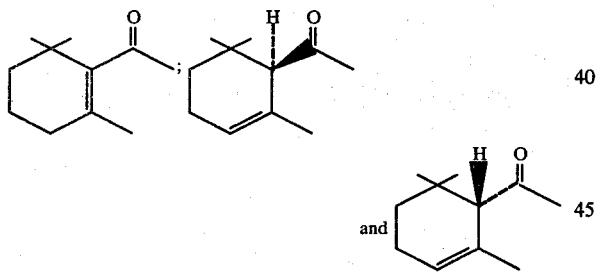

wherein the wavy line is representative of a "cis" or "trans" configuration of the methyl moiety with respect to the acetyl or crotonoyl moiety, both of which are bonded to the cyclohexenyl moiety, the "cis" isomer presumably being the major isomer and the "trans" isomer presumably being the minor isomer in this reaction sequence.

Nothing in the prior art, however, teaches the usefullness of the processes of our invention or the usefullness of the compounds having the structures:

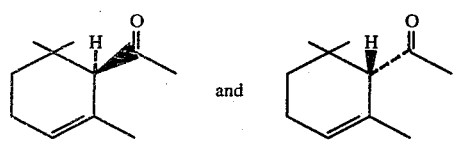

for their organoleptic properties.

for their organoleptic properties.

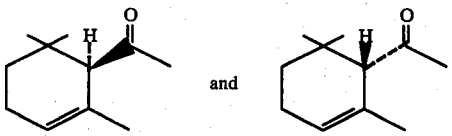

Figure 3:
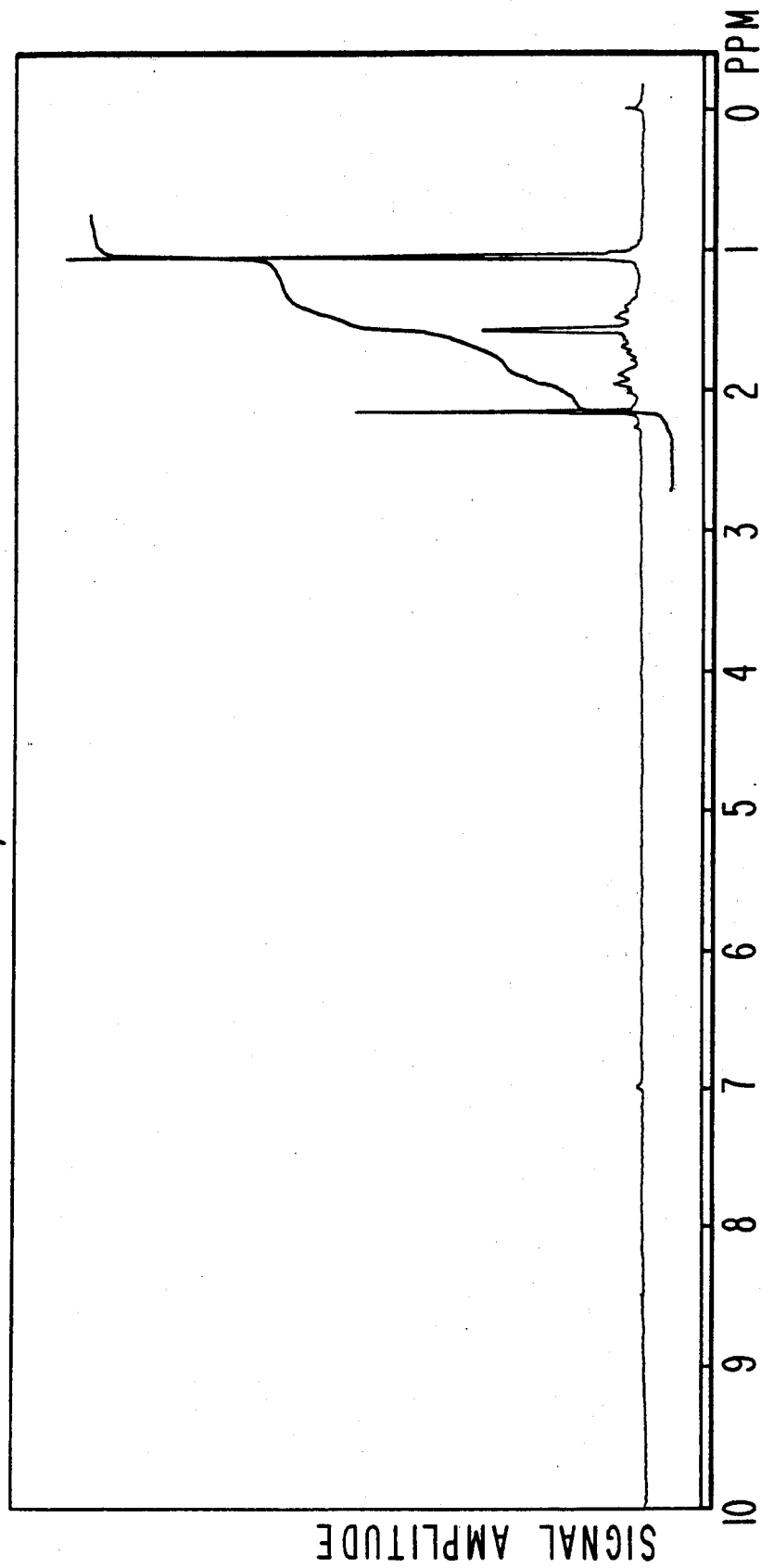

FIG. 3 is the NMR spectrum of the compound of peak 3 of Example I, having the structure:

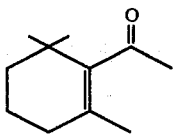

Figure 4:
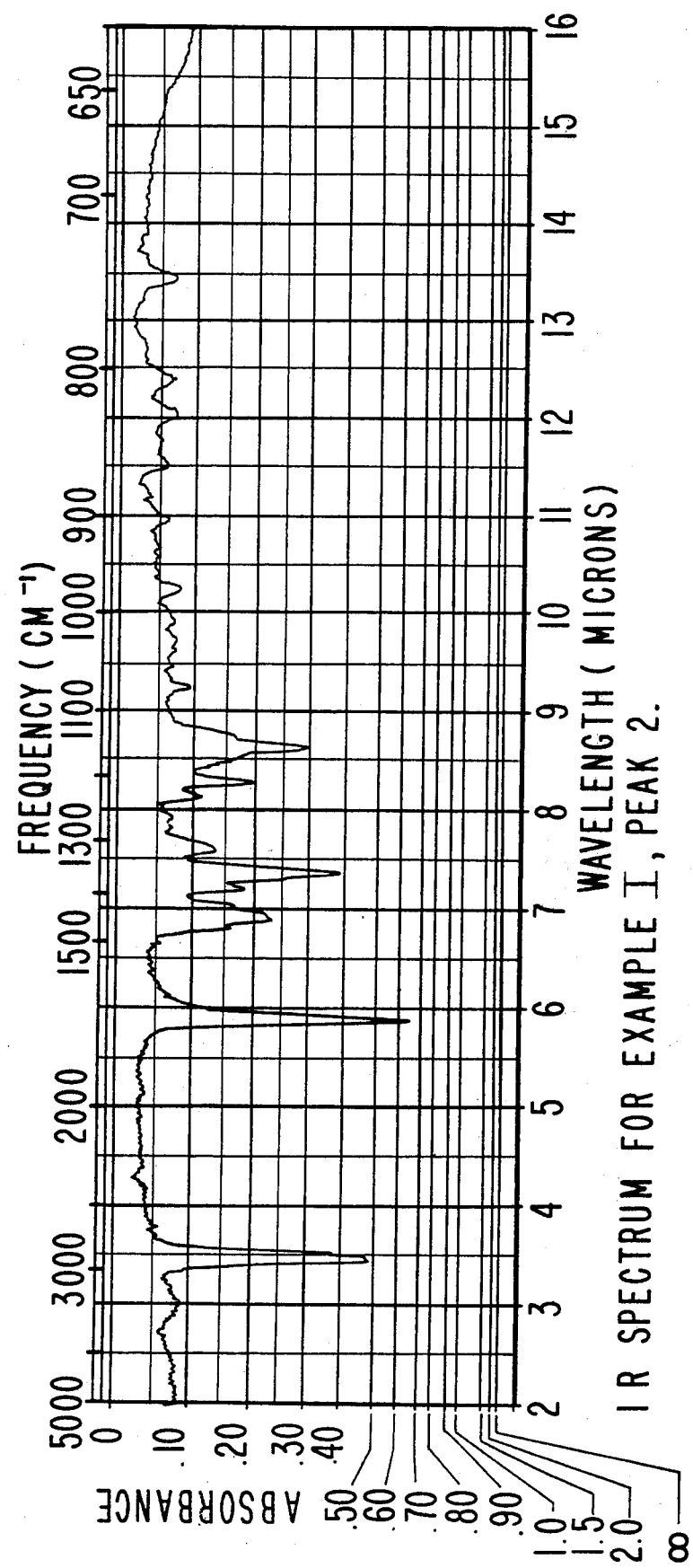

FIG. 4 is the infrared spectrum for the compounds of peak 2 of Example I containing compounds having the structures:

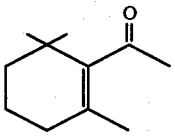

Figure 5:
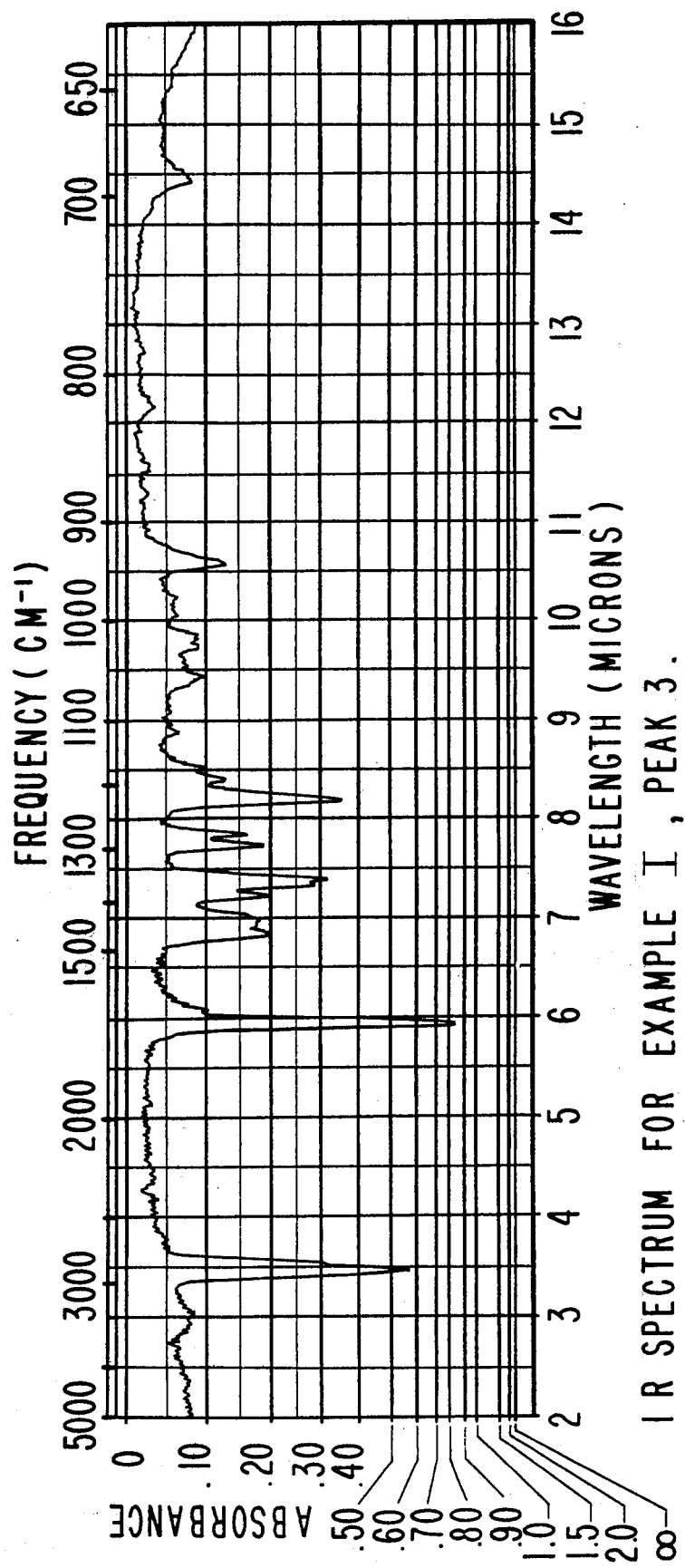

FIG. 5 is the infrared spectrum for peak 3 of Example I having the compound having the structure:

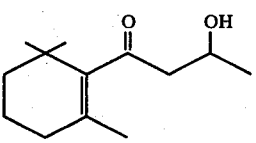

Figure 6:
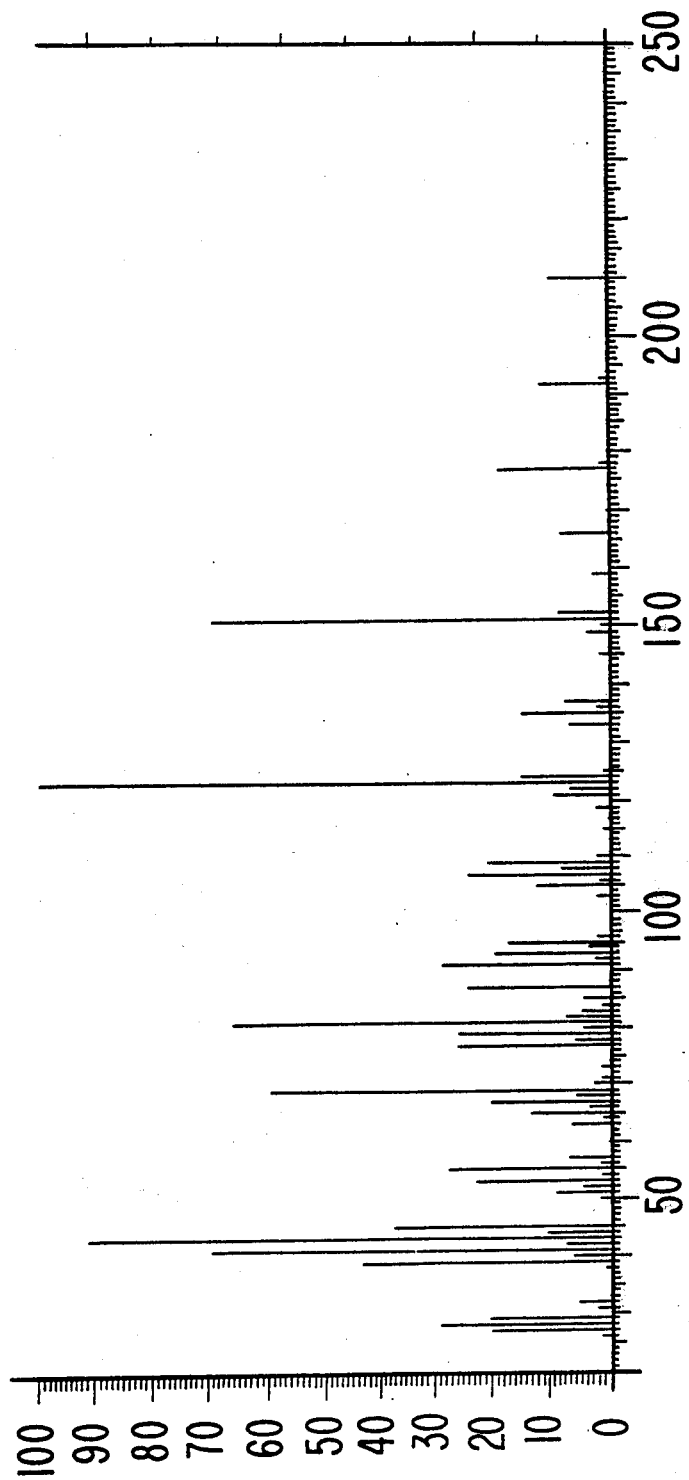

FIG. 6 is the mass spectrum for peak 2 of Example II containing essentially compounds having the structures:

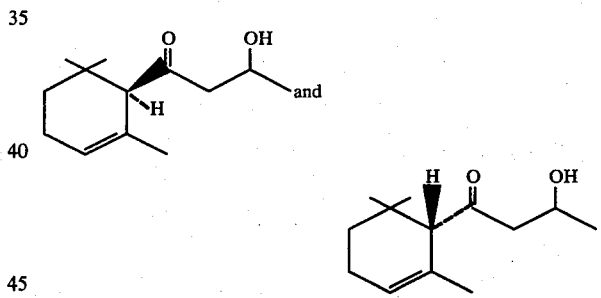

Figure 7:
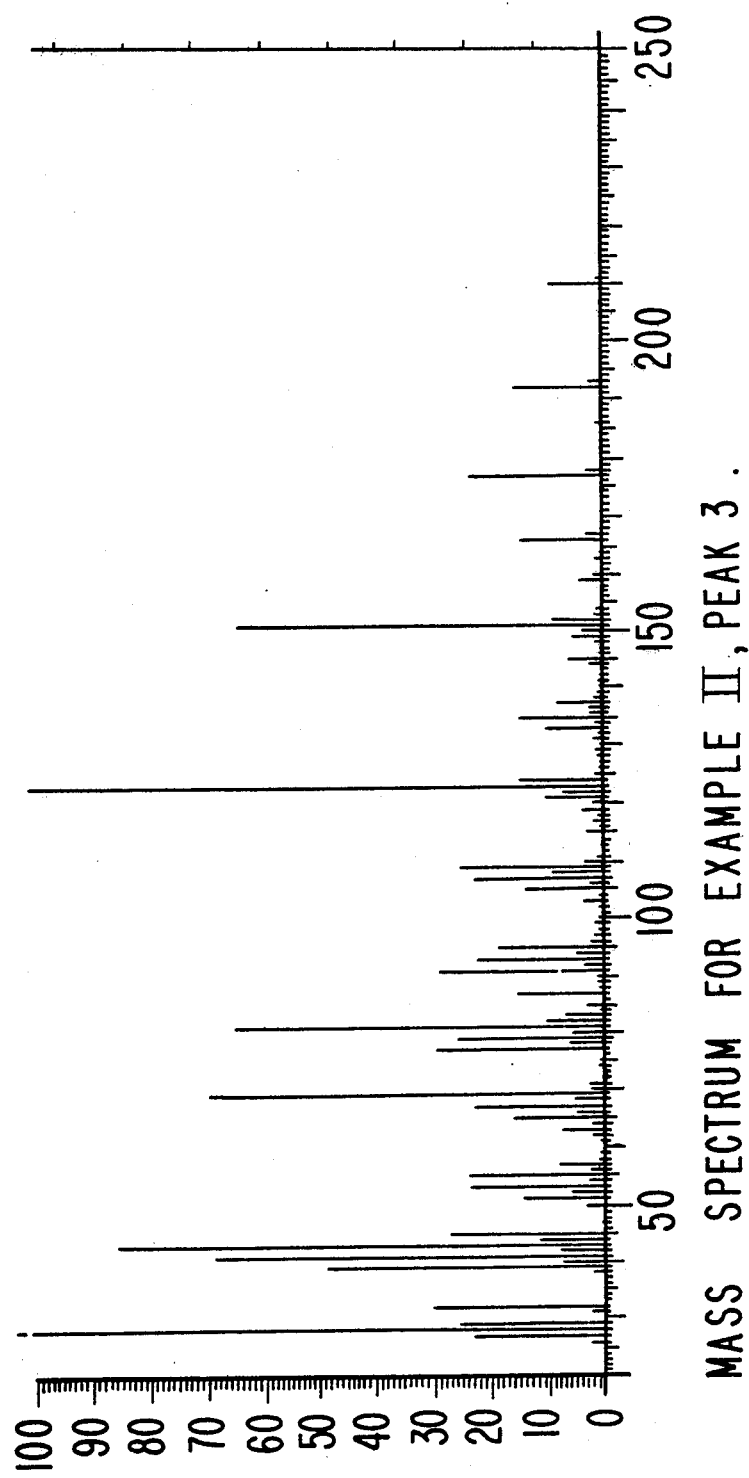

FIG. 7 is the mass spectrum for peak 3 of Example II consisting essentially of a compound having the structure:

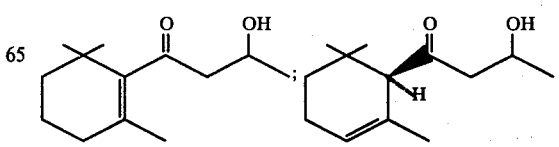

Figure 8:
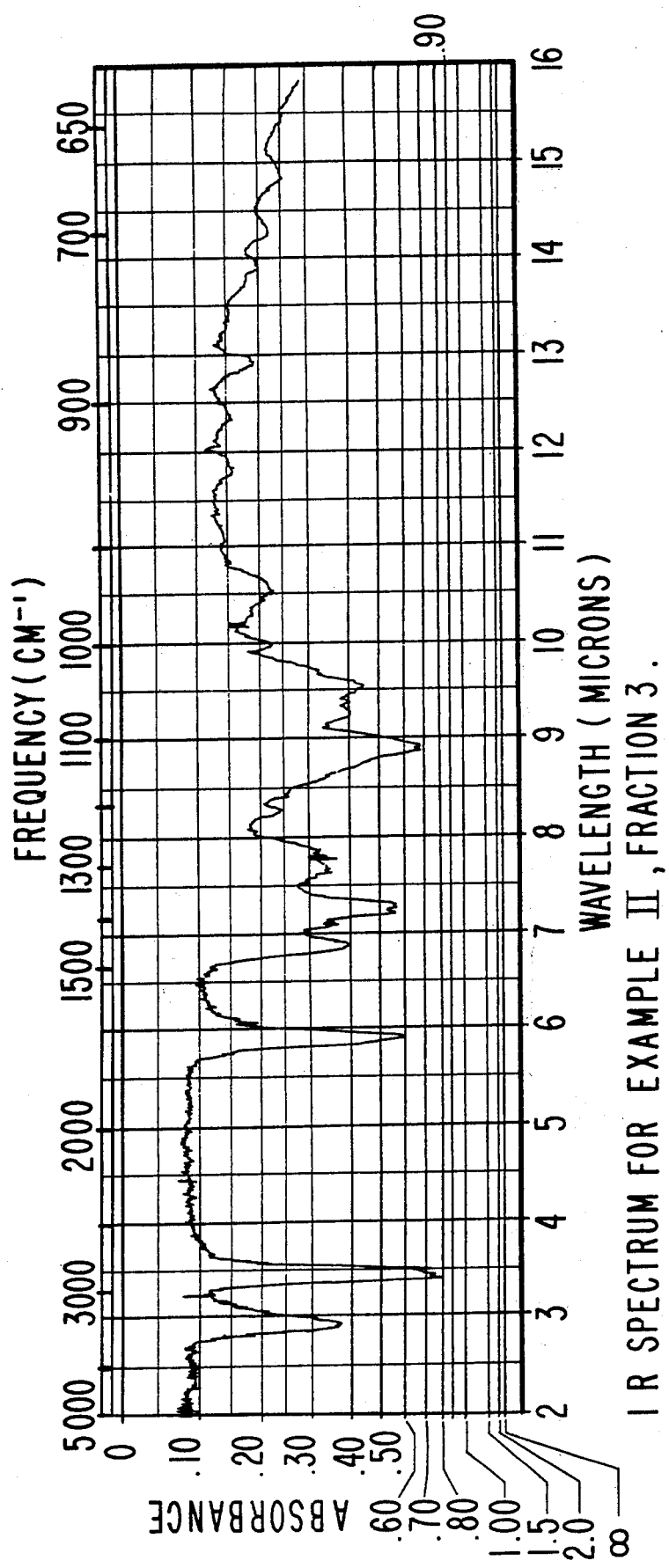

FIG. 8 is the infrared spectrum for distillation fraction 3 of Example II containing compounds having the structures:

-continued

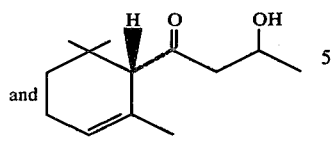

FIG. 9 is the NMR spectrum for distillation fraction 3 of the reaction product of Example II containing compounds having the structures:

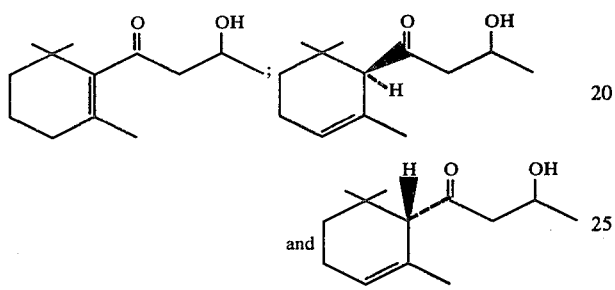

THE INVENTION

The present invention provides compounds having the generic structure:

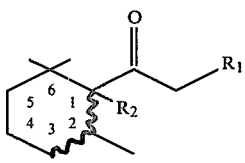

wherein $R_1$ is hydrogen or ethylidene having the structure:

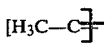

$R_2$ is hydrogen or no group; one of the wavy lines is a carbon-carbon double bond and the other of the wavy lines is a carbon-carbon single bond; with the proviso that when the $\Delta^{2,3}$ bond is a carbon-carbon double bond then $R_2$ is hydrogen and $R_2$ and the moiety:

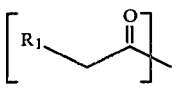

are so juxtaposed that the molecule:

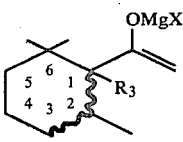

exists in two different isomeric forms; a "+" and a "−" form. The present invention also provides intermediates having the generic structure:

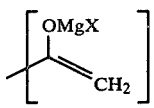

wherein X is chloro, bromo or iodo and $R_3$ is hydrogen or no group; and one of the wavy lines is a carbon-carbon double bond and the other of the wavy lines is a carbon-carbon single bond; with the proviso that when the $\Delta^{2,3}$ is a carbon-carbon double bond then $R_3$ is hydrogen and $R_3$ and the moiety:

$$\left[ \begin{array}{c} \text{OMgX} \\ \diagup \\ \diagdown \text{CH}_2 \end{array} \right]$$

are so juxtaposed that the molecule having the structure:

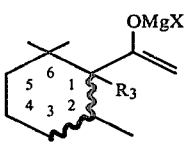

exists in two different isomeric forms; a "+" form and a "−" form. The present invention also provides processes for preparing such compounds and intermediates using the compound having the structure:

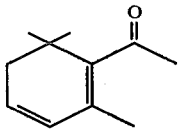

as a precursor. Such a process is summarized and illustrated by the reaction sequence:

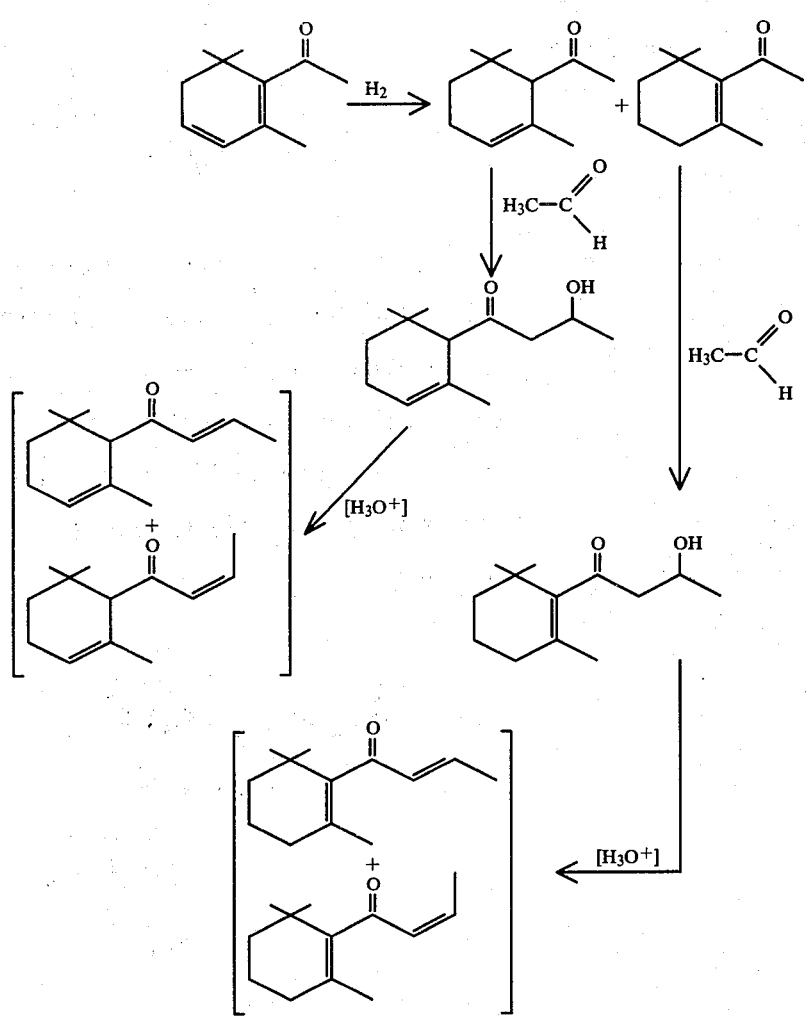

The 1-acyl-2,6,6-trimethylcyclohexene derivatives of our invention produced according to the process of our invention are capable of augmenting or enhancing mint, lemon and tropical fruit flavors by imparting thereto herbaceous, earthy, patchouli-like, damascenone-like, lemony and minty aroma and flavor characteristics.

The 1-acyl-2,6,6-trimethylcyclohexene derivatives of our invention as well as mixtures thereof are also capable of modifying or enhancing the odor characteristics of perfume compositions, colognes and perfumed articles (including soaps, nonionic, anionic and cationic detergents and fabric softener articles) by imparting thereto sweet, floral, fruity, rose-like and minty/camphoraceous aromas with floral, hay-like and musty background notes and tobacco nuances, thus fulfilling a need in the field of perfumery.

In tobacco, tobacco flavoring compositions, substitute tobacco and substitute tobacco flavoring compositions, the 1-acyl-2,6,6-trimethylcyclohexene derivatives of our invention produced according to the process of our invention impart musty-floral, slightly sweet, fruity and damascenone-like aroma notes to tobacco and substitute tobaccos prior to smoking and sweet, Virginia-like tobacco notes to tobacco on smoking in the main stream and in the side stream.

The 1-acyl-2,6,6,-trimethylcyclohexene derivatives of our invention are produced by first reacting 2,6,6-trimethyl-1-acetyl-cyclohexene-1 having the structure:

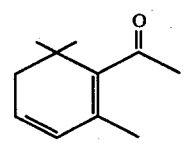

with hydrogen over a catalyst such as a Lindlar catalyst (palladium suspended on calcium carbonate) thus forming a mixture of 1-acetyl-2,6,6-trimethylcyclohexene-1 and cyclohexene-2 compounds. This resulting mixture of compounds having the structures:

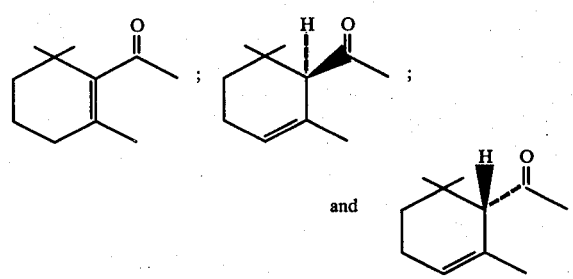

may either be separated whereupon the resulting substantially pure organic compounds can be used "as is" for their organoleptic properties or the resulting substantially pure organic compounds can be further reacted. On the other hand, the resulting mixture can be used as is as an intermediate or for its organoleptic properties. In any event, the 1-acetyl-2,6,6-trimethylcyclohexene-1 and/or 2 derivatives thus produced may be individually or in admixture further reacted with a lower alkyl magnesium halide (lower alkyl Grignard reagent) in order to produce an organometallic salt having the structure:

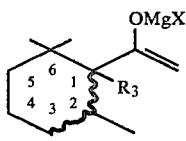

wherein X is chloro, bromo or iodo; $R_3$ is hydrogen or no group; wherein one of the wavy lines is a carbon-carbon double bond and the other of the wavy lines is a carbon-carbon single bond; with the proviso that when the $\alpha^{2,3}$ bond is a carbon-carbon double bond, then $R_3$ is hydrogen and $R_3$ and the moiety:

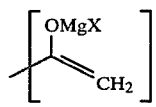

are so juxtaposed that the molecule:

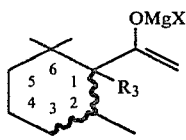

exists in two different forms, a "+" and a "−" form. The resulting organometallic compound(s) is (are) then reacted with acetaldehyde followed by hydrolysis in order to produce compounds either in pure form or in admixture (depending on whether the starting materials are in "pure form" or in "admixture") having one or more of the structures:

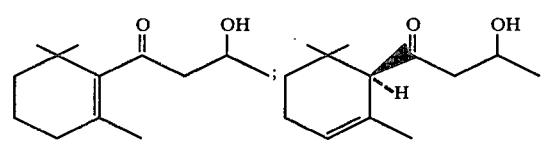

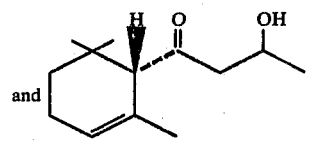

The resulting hydroxy ketone derivatives can be separated (as by distillation) and used for their organoleptic properties individually or they can be separated and further reacted (e.g., dehydrated) or they can be utilized "as is" in admixture for their organoleptic properties. When the resulting hydroxy ketones having the structures:

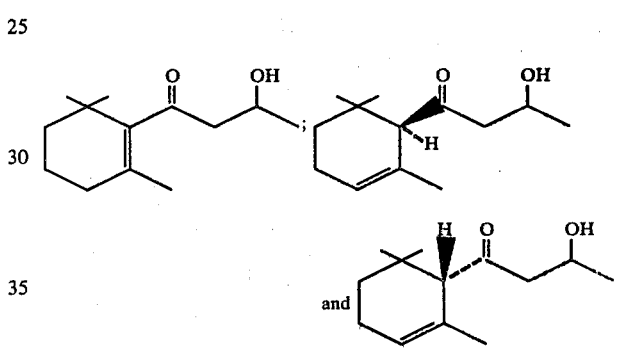

are either separately or in admixture dehydrated, each of the compounds or the compounds in admixture gives rise to compounds having the structures:

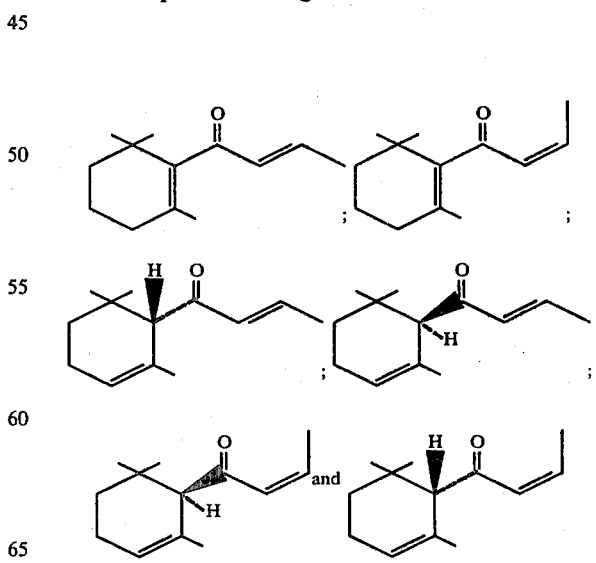

The over-all reaction sequence is as follows:

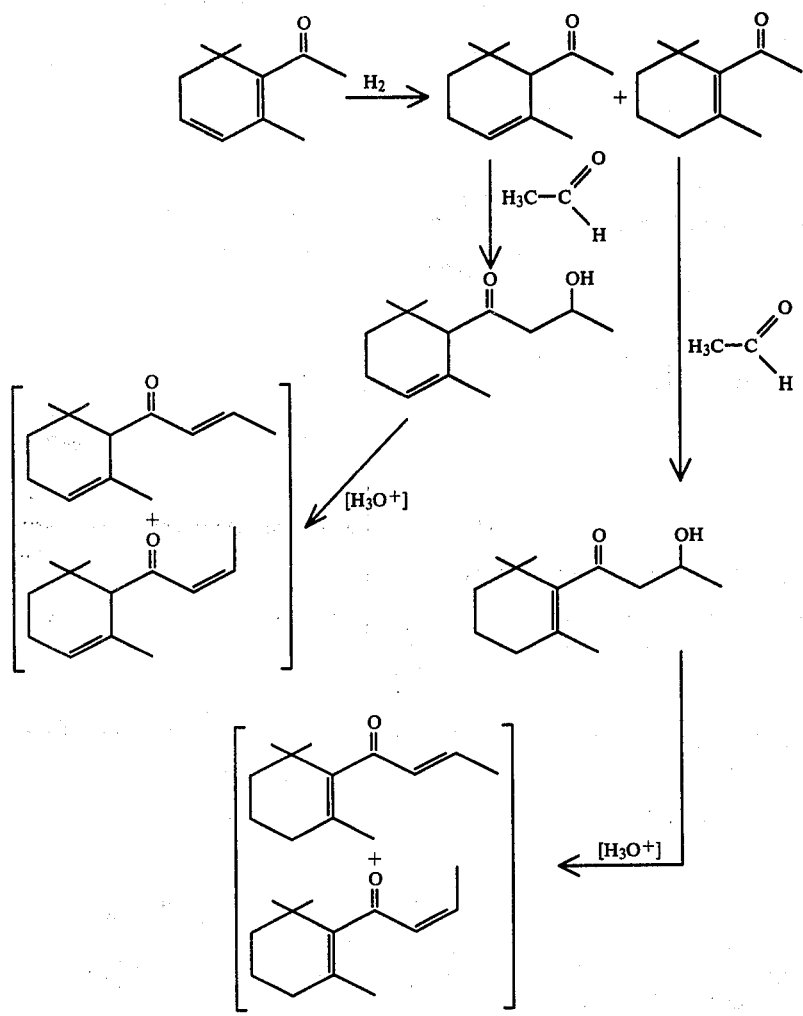

In carrying out the hydrogenation of the 2,6,6-trimethyl-1-acetyl-1,3-cyclohexadiene according to the reaction scheme:

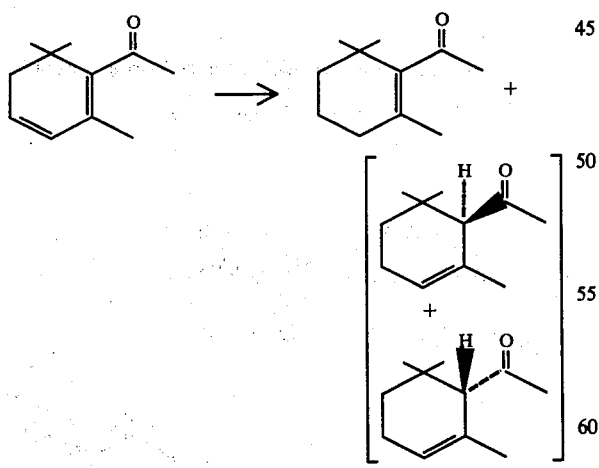

The hydrogenation is carried out at a temperature in the range of from 0° C. up to 100° C. at pressures of from about 1 atmosphere up to about 100 atmospheres using catalysts such as palladium (from 1% up to 10%) on barium sulfate or palladium (from 1% up to 10%) on calcium carbonate in the presence of inert solvents, such as ethyl acetate and catalyst promoters, such as quinoline.

The mole ratio of catalyst:catalyst promoter, e.g., palladium on barium sulfate:quinoline is preferably about 1:1 (weight:weight) but ratios of catalyst:promoter may vary from about 0.25:1 up to about 1:0.25. The weight ratio of 2,6,6,-trimethyl-1-acetyl-1,3-cyclohexadiene: inert solvent (e.g., ethyl acetate) may vary from about 1:1 up to about 1:20 with a ratio of about 1:10 (weight:weight) being preferred. At the end of the reaction, the reaction product may, if desired, by separated whereby the compounds having the structures:

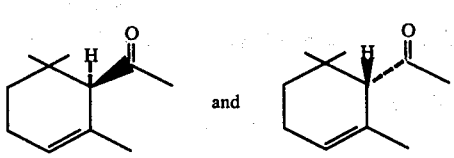

may be separated from the compound having the structure:

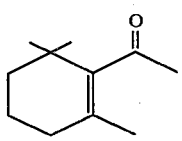

as by fractional distillation. The separation of the stereo-isomers having the structures:

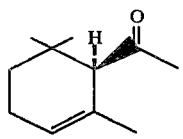 and 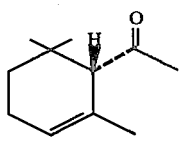

requires a more complicated process, e.g., as by forming "++" or "+−" stereospecific oxime reaction products of the ketones with stereoisomeric amines (e.g., [+] 3-amino-2-methoxy propionic acid ethyl ester having the structure:

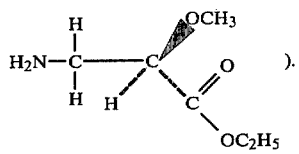

An example of a Shiff base with, for example, (+) 2,6,6-trimethyl-1-acetyl-1,3-cyclohexadiene has the structure:

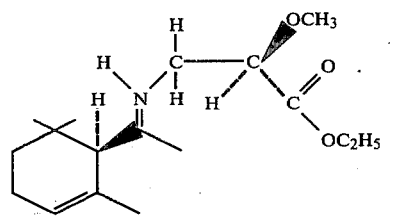

The resulting mixture of stereoisomers can then be separated as by column chromatography on a silica gel column.

The resulting mixture of 2,6,6-trimethyl-1-acetylcyclohexenes is then reacted, if desired, with a lower $C_1$-$C_6$ alkyl Grignard reagent having the structure:

RMgX wherein X is halogen selected from the group consisting of chloro, bromo and iodo whereby a mixture of organometallic compounds is formed having the structures:

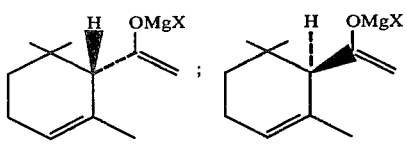

On the other hand, one of the Grignard reagents having the structures:

R—MgX may be reacted after separation with one of the compounds having the structures:

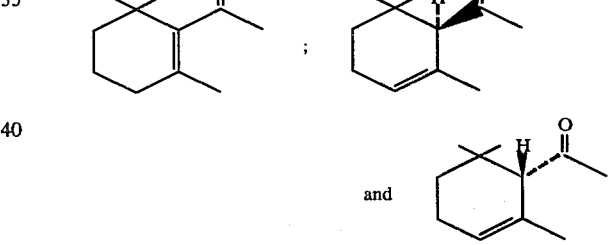

thereby forming a substantially "pure" organometallic compound having one of the structures:

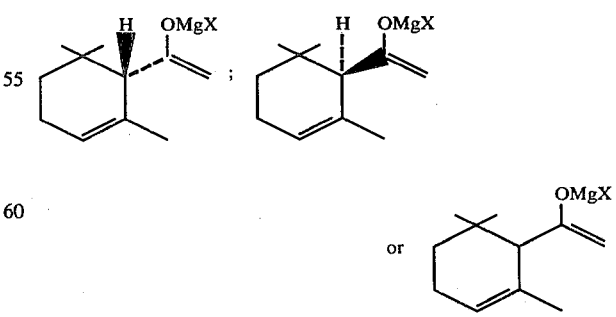

The reaction sequence is illustrated according to the following reaction:

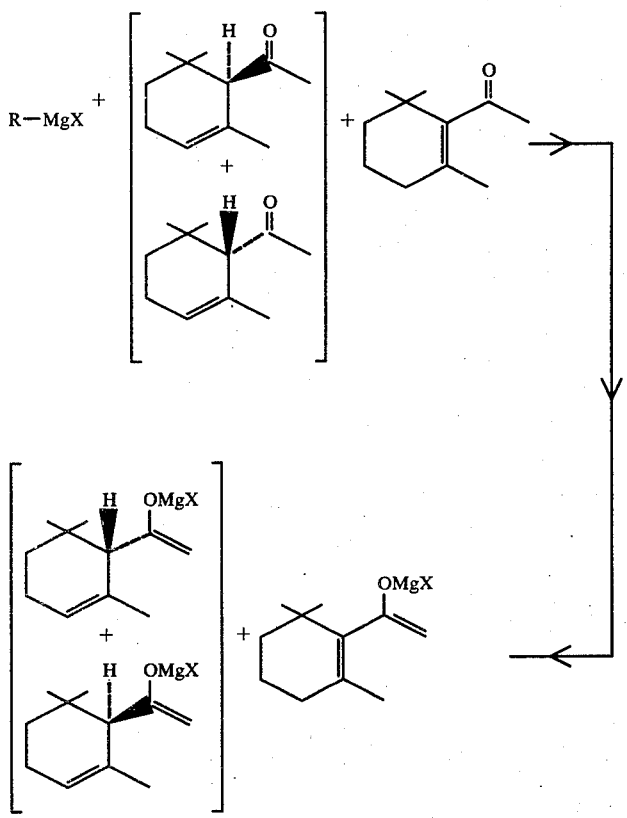

wherein R is $C_1$–$C_6$ lower alkyl and wherein X is halogen selected from the group consisting of chloro, bromo and iodo. This reaction of the lower alkyl Grignard reagent with the 2,6,6-trimethyl-1-acetyl cyclohexene derivative is carried out in the presence of a solvent which is inert in the reaction mass, for example, diethyl ether or tetrahydrofuran. The reaction temperature is preferably between 20° and 35° C. at atmospheric pressure. Higher pressures or lower pressures and higher temperatures and lower temperatures may be used but there is no advantage to so using the temperature outside of 20°–35° C. and pressures outside of one atmosphere (ambient conditions).

After the organometallic compound having the structures:

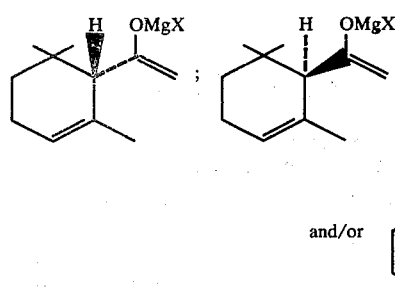

are formed the resulting mixture or individual organometallic compound is reacted with acetaldehyde and then water to form a hydroxy ketone or mixture of hydroxy ketones having one or more of the following structures:

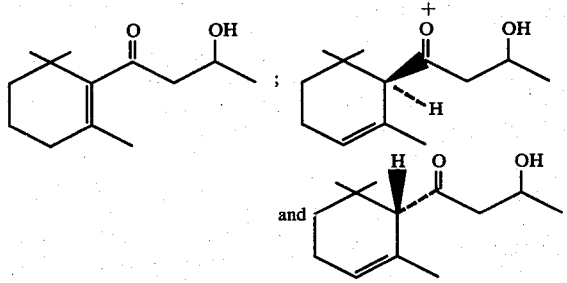

The reaction sequence for the reaction of acetaldehyde with one or more of the organometallic compounds having one of the structures:

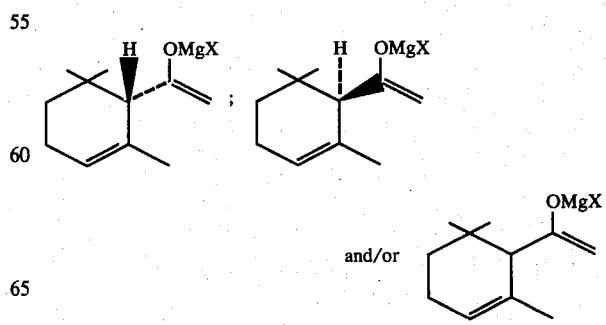

is as follows:

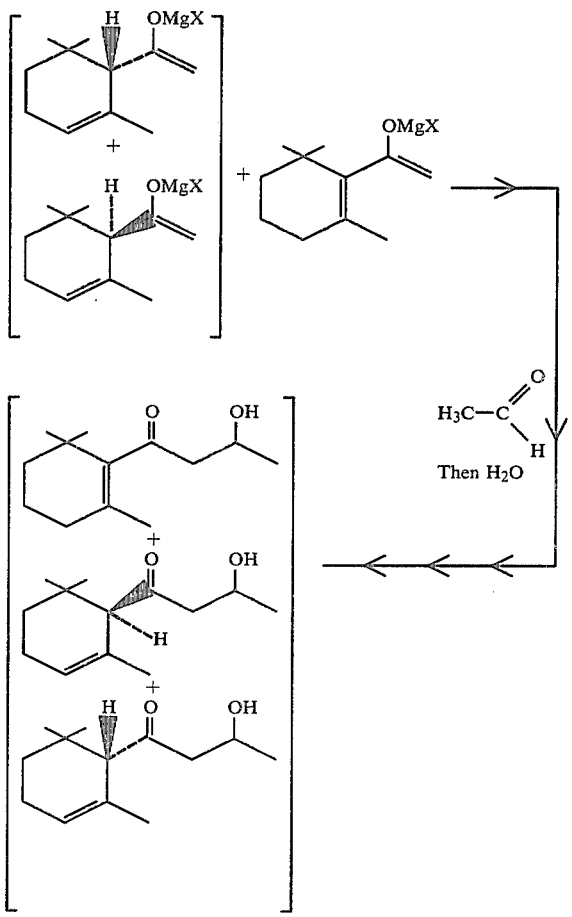

The reaction temperature for this reaction is preferably between 010° C. and +15° C.; more preferably between 0° C. and 10° C. at atmospheric pressure. The acetaldehyde is added to one or more of the compounds having the structures:

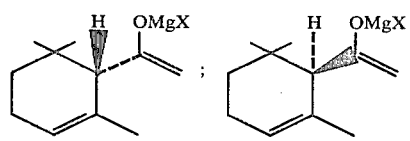

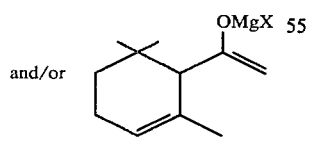

in admixture is an inert solvent such as toluene or xylene. It is preferred that the weight ratio of inert solvent such as toluene or xylene:acetaldehyde be in the range of from about 2:1 up to about 5:1 with a preferred weight ratio of solvent such as toluene or xylene: acetaldehyde being about 3–4:1. After completion of the reaction of one or more of the organometallic compounds having one of the structures:

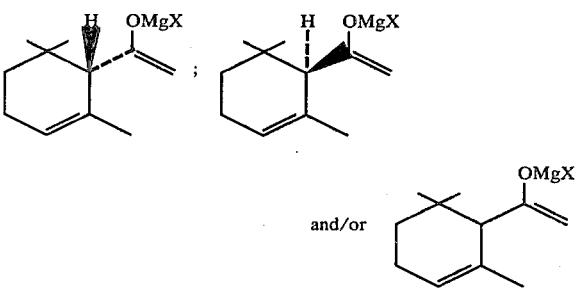

with acetaldehyde, the resulting reaction product is then admixed with water at a temperature of between 10° C. and 40° C., preferably between 15° C. and 25° C. at one atmosphere pressure.

The resulting compound, the hydroxy ketone or mixture of hydroxy ketones having one or more of the structures:

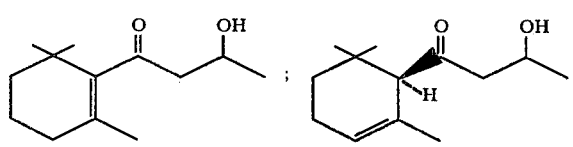

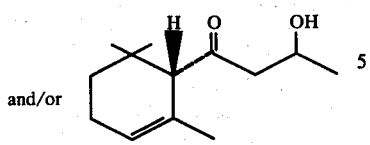

and/or may be separated as by fractional distillation whereby the compounds having the structures:

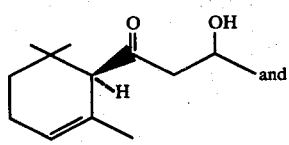
and

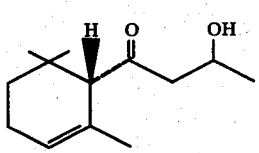

may be separated from the compound having the structure:

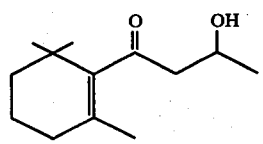

The compounds having the structures:

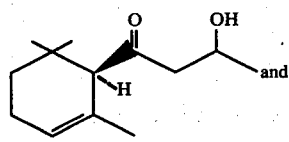
and

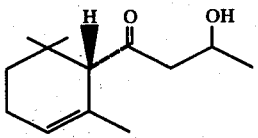

may also be separated by first forming Shiff bases thereof with such materials as +3-amino-2-methoxy-propionic acid ethyl ester having the structure:

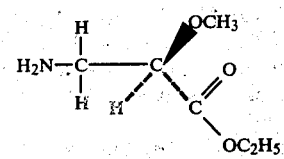

whereby such compounds are formed as have the structure:

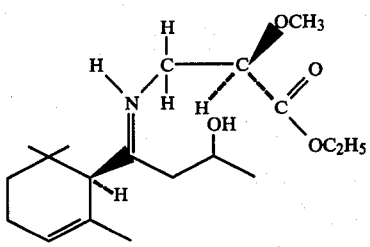

The Shiff bases may then be separated as by column chromatography and the individual stereoisomers may then be hydrolyzed to form the pure stereoisomers.

In the alternative, one or more of the compounds having the structures:

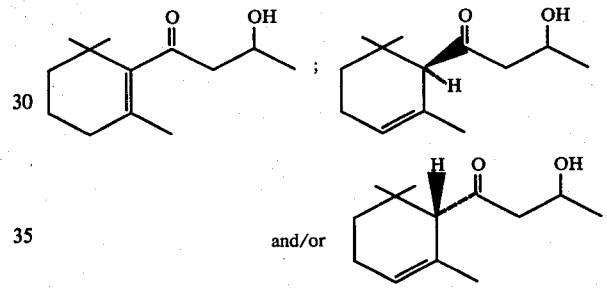

and/or may be dehydrated with a dehydrating agent, such as acetic anhydride whereby α and/or β-damascone isomers may be formed having one or more of the structures:

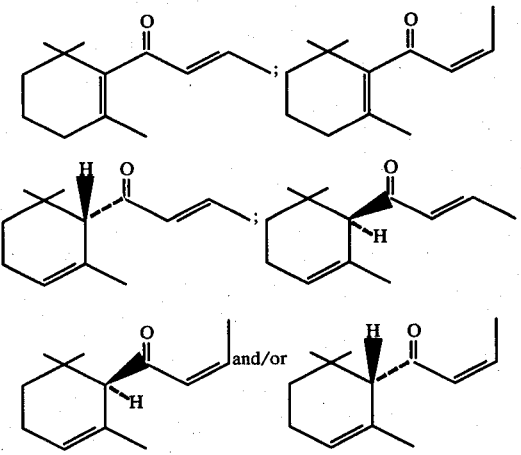

The reaction sequence for their dehydration reaction is as follows:

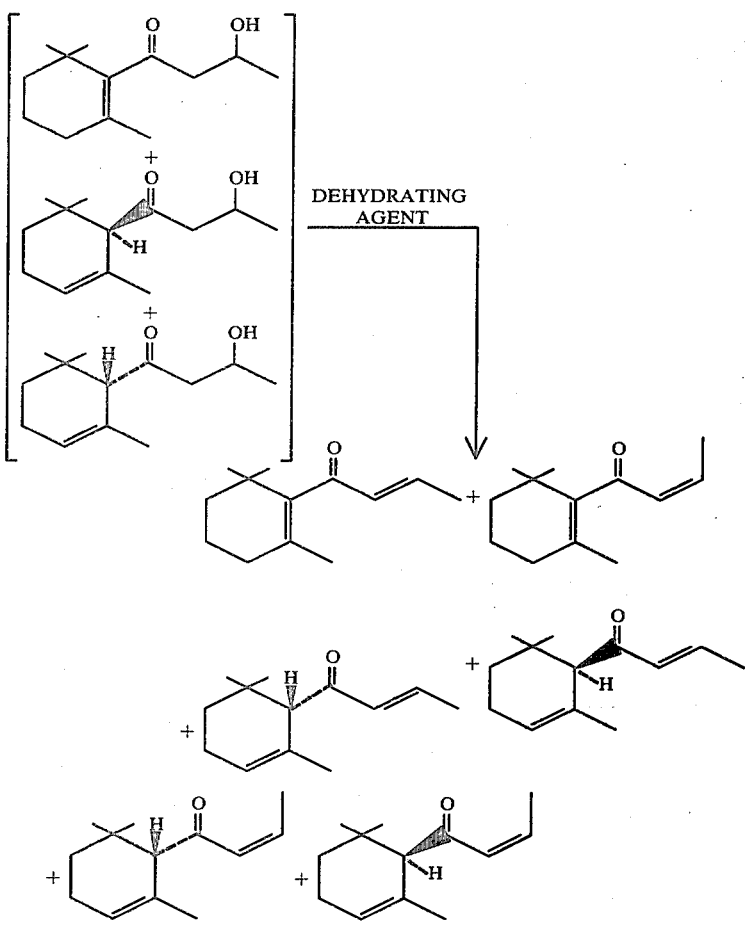

The dehydration reaction takes place in the presence of an inert solvent, such as toluene or xylene and the dehydration reagent is a compound such as acetic anhydride, phosphoric acid or para toluene sulfonic acid. The dehydration also takes place in the presence of a weak base, such as sodium acetate, potassium acetate, sodium carbonate or potassium carbonate. The weight ratio of keto alcohol:solvent may vary from 1:0.5 (keto alcohol): solvent/weight:weight) up to 1:10 with a preferred ratio of between 1:0.5 and 1:1. The mole ratio of keto alcohol: dehydrating agent is preferably between 1:0.25 and 1:1 (keto alcohol:dehydrating agent) and the weight ratio of dehydrating agent:weak base is preferably between 1:1 and b 10:1 with a ratio of from 4:1 up to 5:1 dehydrating agent:weak base being preferred.

At the point of completion of the reaction, the reaction mass is "worked up" and the isomers, the cis and trans isomers, and the "α" and "β" isomers are separated by fractional distillation. On the other hand, the stereoisomers must be separated only after reaction thereof with stereoisomeric separation reagents, such as (+)3-aino-2-methoxypropionic acid ethyl ester having the structure:

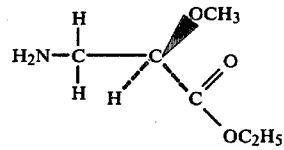

to form such Shiff bases as have the structure:

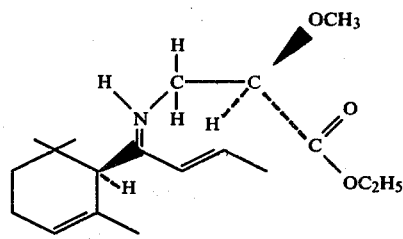

When the 1-acyl-2,6,6-trimethylcyclohexene derivatives according to the process of our invention are used as food flavor adjuvants, the nature of the co-ingredients included with the 1-acyl-2,6,6-trimethylcyclohexene derivatives used in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the 1-acyl-2,6,6-trimethylcyclohexene derivatives produced according to the process of our invention and in addition sweetening agents which may be sugars, including sucrose or dextrose and/or artificial sweeteners such as cyclamates or saccharin. Other optional ingredients may also be present.

Substances suitable for use herein as co-ingredients or flavoring adjuvants as well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2-and 3-tertiary-butyl-4-hydroxy-anisole), butylated hydroxy toluene (2,6-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benazaldehyde, $\beta$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as δ nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the acyl-2,6,6-trimethylcyclohexene derivatives of our invention by not covering or spoiling the organoleptic properties (aroma and/or taste) thereof, (ii) be non-reactive with the acyl-2,6,6-trimethylcyclohexene derivatives of our invention and (iii) be capable of providing an environment in which the acyl-2,6,6-trimethylcyclohexene derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1-acyl-2,6,6-trimethylcyclohexene derivatives of our invention employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of one or more 1-acyl-2,6,6-trimethylcyclohexene derivatives of our invention will, of course, substantially vitiate any possibility of obtaining the desired results while excess quantities prove needlessly costly and in extreme cases, may disrupt the flavor-aroma balance, thus providing self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of one or more 1-acyl-2,6,6-trimethylcyclohexene derivatives of our invention ranging from a small but effective amount, e.g., about 0.5 parts per million up to about 100 parts per million based on total food composition or chewing gum composition or medicinal product composition or toothpaste composition are suitable. Concentrations in excess of the maximum quantity stated are not normally recommended since they fail to provide commensurate enhancement of organoleptic properties. In those instances, where one or more 1-acyl-2,6,6-trimethylcyclohexene derivatives of our invention is added to the foodstuff as an integral component of a flavoring composition, it is, of course, essential that the total quantity of flavoring composition employed be sufficient to yield an effective concentration of one or more 1-acyl-2,6,6-trimethylcyclohexene derivatives of our invention in the foodstuff product.

Food flavoring compositions containing one or more of the compounds prepared in accordance with the present invention preferably contain one or more 1-acyl-2,6,6-trimethylcyclohexene derivatives in concentrations ranging from about 0.02% up to about 15% by weight based on the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more 1-acyl-2,6,6-trimethylcyclohexene derivatives prepared in accordance with our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and one or more 1-acyl-2,6,6-trimethylcyclohexene derivatives or our invention in a dry blender until the requisite degree of uniformity is achieved.

It is presently preferred to combine one or more 1-acyl-2,6,6-trimethylcyclohexene derivatives of our invention with at least one of the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl Acetate;
Isobutyl acetate;
Cuminaldehyde;
Alpha ionone;
Cinnamyl formate;
Ethyl butyrate;
Methyl cinnamate;
Acetic acid;

Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,6,6-trimethylcyclohex-1-ene);
β-Damascenone (1-crotonyl-2,6,6-trimethylcyclohexa-1,3-diene);
Beta-cyclohomocitral (2,6,6-trimethylcyclohex-1-ene carboxaldehyde)
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene One or more 1-acyl-2,6,6-trimethylcyclohexene derivatives prepared in accordance with the process of our invention and one or more auxiliary perfume ingredients including, for example, alcohols, aldehydes, ketones, other than the 1-acyl-2,6,6-trimethylcyclohexene derivatives of our invention, terpinic hydrocarbons, nitriles, esters, lactones, natural essential oils and synthetic essential oils, may be admixed so that the combined odors of the individual components produce a pleasant and desired fragrance, particularly, and preferably, in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, one or more 1-acyl-2,6,6-trimethylcyclohexene derivatives prepared in accordance with the process of our invention can be used to alter, modify, or enhance the aroma characteristics of a perfume composition, for example, by utilizing or moderating the olfactory reaction contributed by another ingredient in the composition.

The amount of one or more 1-acyl-2,6,6-trimethylcyclohexene derivatives prepared in accordance with the process of our invention which will be effective in perfume compositions as well as in perfumed articles (e.g., anionic, nonionic and cationic detergents, soaps, and fabric softener compositions and articles) and colognes depends upon many factors, including the other ingredients, their amounts and the effects which are desired. It has been found that perfume compositions containing as little as 0.01% of one or more 1-acyl-2,6,6-trimethylcyclohexene derivatives prepared in accordance with the process of our invention and less than 50% of one or more 1-acyl-2,6,6-trimethylcyclohexene derivatives prepared in accordance with the process of our invention or even less (e.g., 0.005%) can be used to impart a sweet, floral, fruity, rose-like, minty/camphoraceous aroma with a floral, hay-like, musty background and tobacco nuance to soaps, cosmetics, anionic, cationic or nonionic detergents, fabric softener compositions, fabric softener articles or other products. The amount employed can range up to 70% of the fragrance components and will depend on considerations of cost, nature of the end product, the effect desired on the finished product and the particular fragrance sought.

One or more 1-acyl-2,6,6-trimethylcyclohexene derivatives prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 0.2% of one or more 1-acyl-2,6,6-trimethylcyclohexene derivatives prepared in accordance with the process of our invention will suffice to impart an intense weak, floral, fruity, rose-like and minty/camphoraceous aroma to rose formulations. Generally, no more than 6% of one or more 1-acyl-2,6,6-trimethylcyclohexene derivatives of our composition based on the ultimate end product is required in the perfumed article composition.

In addition, the perfume composition or fragrance composition of our invention can contain a vehicle or carrier for one or more 1-acyl-2,6,6-trimethylcyclohexene derivatives prepared in accordance with the process of our invention. The vehicle can be a liquid, such as a non-toxic alcohol, a non-toxic glycol, or the like. The carrier can also be an absorbent solid, such as a gum (e.g., gum arabic) or components for encapsulating the composition (such as gelatin) as by coacervation.

It will thus be apparent that one or more 1-acyl-2,6,6-trimethylcyclohexene derivatives prepared in accordance with the process of our invention can be utilized to alter, modify or enhance sensory properties, particularly organoleptic properties, such as flavor(s) and/or fragrance(s) of a wide variety of consumable materials.

Furthermore, one or more 1-acyl-2,6,6-trimethylcyclohexene derivatives prepared in accordance with the process of our invention are capable of supplying and/or potentiating certain flavor and aroma notes usually lacking many smoking tobacco flavors and substitute tobacco flavors heretofore provided.

As used herein in regard to smoking tobacco flavors, the terms "alter" and "modify" in their various forms mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired musty-floral, slightly sweet, fruity, damascenone-like aroma and taste nuances prior to smoking and sweet, Virginia tobacco-like notes on smoking in the main stream and in the side stream are created or enhanced and may be readily controlled and maintained at the desired uniform level regardless of variations in the tobacco components of the blend.

This invention further provides improved smoking tobacco additives and methods whereby various musty-floral, slightly sweet, fruity, damascenone notes prior to smoking and sweet, Virginia tobacco-like notes are imparted (on smoking in the main stream and the side stream) to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one 1-acyl-2,6,6-trimethylcyclohexene derivative prepared according to the process of our invention In addition to the one or more 1-acyl-2,6,6-trimethylcyclohexene derivatives prepared in accordance to the process of our invention, other flavoring and aroma additives may be added to the smoking tobacco materials or substitute therefor either separately or in admixture with the one or more 1-acyl-2,6,6-trimethylcyclohexene derivatives prepared in accordance to the process of our invention as follows:

(i) Synthetic Materials

Beta-ethyl-cinnamaldehyde;
Beta-cyclohomocitral;
Eugenol;
Dipentene;
β-Damascenone;
β-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene; -furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot Oil;
Cocoa extract;
Nutmeg oil;
Origanum oil An aroma and flavoring concentrate containing one or more 1-acyl-2,6,6-trimethylcyclohexene derivatives prepared in accordance with the process of our invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the porportion by weight of the sum total of one or more 1-acyl-2,6,6-trimethylcyclohexene derivatives produced to smoking tobacco material is between 250 ppm and 1,500 ppm (0.025%–0.15%) of the active ingredients to the smoking tobacco material. We have further found that satisfactory results are obtained if the proportion by weight of the sum total of one or more 1-acyl-2,6,6-trimethylcyclohexene derivatives prepared in accordance with the process of our invention is between 2,500 and 15,000 ppm (0.25%–1.50%).

Any convenient method for incorporating one or more 1-acyl-2,6,6-trimethylcyclohexene derivatives prepared in accordance with the process of our invention in the tobacco product may be employed. Thus, one or more 1-acyl-2,6,6-trimethylcyclohexene derivatives of our invention taken alone or along with other flavoring additives may be dissolved in a suitable solvent, such as ethanol, pentane, diethyl ether and/or other volatile organic solvents and the resulting solution may either be sprayed on the cured, cased and blended tobacco material or the tobacco material may be dipped into such solution. Under certain circumstances, a solution containing one or more 1-aceyl-2,6,6-trimethylcyclohexene derivatives prepared in accordance with the process of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or more 1-acyl-2,6,6-trimethylcyclohexene derivatives prepared in accordance with the process of our invention in excess of the amounts or concentrations above-indicated so that when blended with other tobaccos, the final product will have the percentage within the indicated range.

In accordance with one specific example of our invention, an aged, cured and shredded domestic Burley tobacco is sprayed with a 20% ethyl alcohol solution of substantially pure 2,6,6-trimethylyl-1-acetyl-1-cyclohexene in an amount to provide a tobacco composition containing 800 ppm by weight of said 2,6,6-trimethyl-1-acetyl-2-cyclohexene on a dry basis.

Thereafter the alcohol is removed by evaporation and the tobacco is manufactured into cigarettes by the usual techniques. The cigarette when treated as indicated has a desired and pleasing aroma prior to smoking which can be described as musty-floral, slightly sweet, fruity and damascenone-like and on smoking in the main stream and in the side stream, a sweet, Virginia tobacco-like aroma.

While our invention is particularly useful in the manufacture of smoking tobacco, such as cigarette tobacco, cigar tobacco and pipe tobacco, other smoking tobacco products formed from sheeted tobacco dust or fines may also be used. Likewise, one or more 1-acyl-2,6,6-trimethylcyclohexene derivatives prepared in accordance with the process of our invention can be incorporated with materials such as filter tip materials, seam paste, packaging materials and the like which are used along with tobacco to form a product adapted for smoking. Furthermore, one or more 1-acyl-2,6,6-trimethylcyclohexene derivatives prepared in accordance with the process of our invention can be added to certain tobacco lettuce leaves) and, accordingly, by the term "tobacco" as used throughout this specification is meant any composition intended for human consumption by smoking or otherwise, whether composed of tobacco plant parts or substitute materials or both.

The following examples serve to illustrate our invention but our invention is only intended to be limited as indicated in the appended claims. All parts and percentages given herein are by weight unless otherwise specified.

EXAMPLE I

PREPARATION OF 2,6,6-TRIMETHYLCYCLOHEXA-1,3-DIENE WITH HYDROGEN TO FORM 1-ACETYL-2,6,6-TRIMETHYLCYCLOHEXENE-1 AND -2

Reaction:

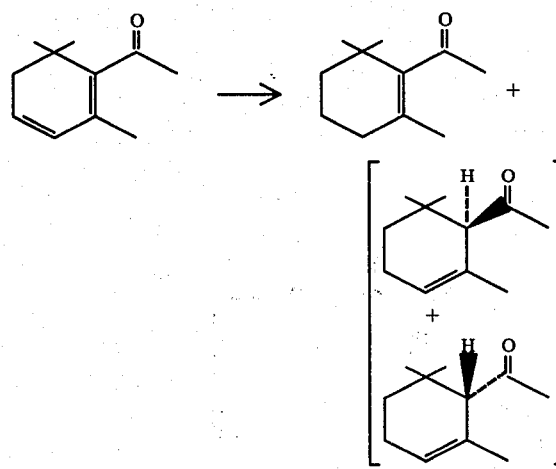

To a 25 ml reaction flask equipped with sample remover system, magnetic stirrer, thermometer and hydrogen addition tube is added 1 gram of 1-acetyl-2,6,6-trimethylcyclohexa-1,3-diene, 10 ml of ethyl acetate and 0.025 grams of quinoline. The resulting mixture is stirred and a reference sample is removed. 0.025 Grams of a catalyst consisting of 5% palladium on barium sulphate is then added and the resulting mixture is hydrogenated to an uptake of 73 ml hydrogen. Hydrogenation is carried out at one atmosphere pressure. NMR, IR and mass spectra analyses yield the information that the resulting material contains compounds having the structures:

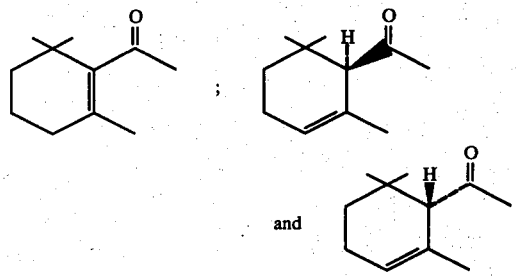

30% of the reaction mass contains compounds having the structures:

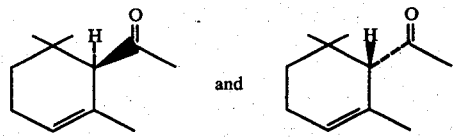

60% of the reaction mass contains a compound having the structure:

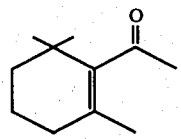

Figure 1:
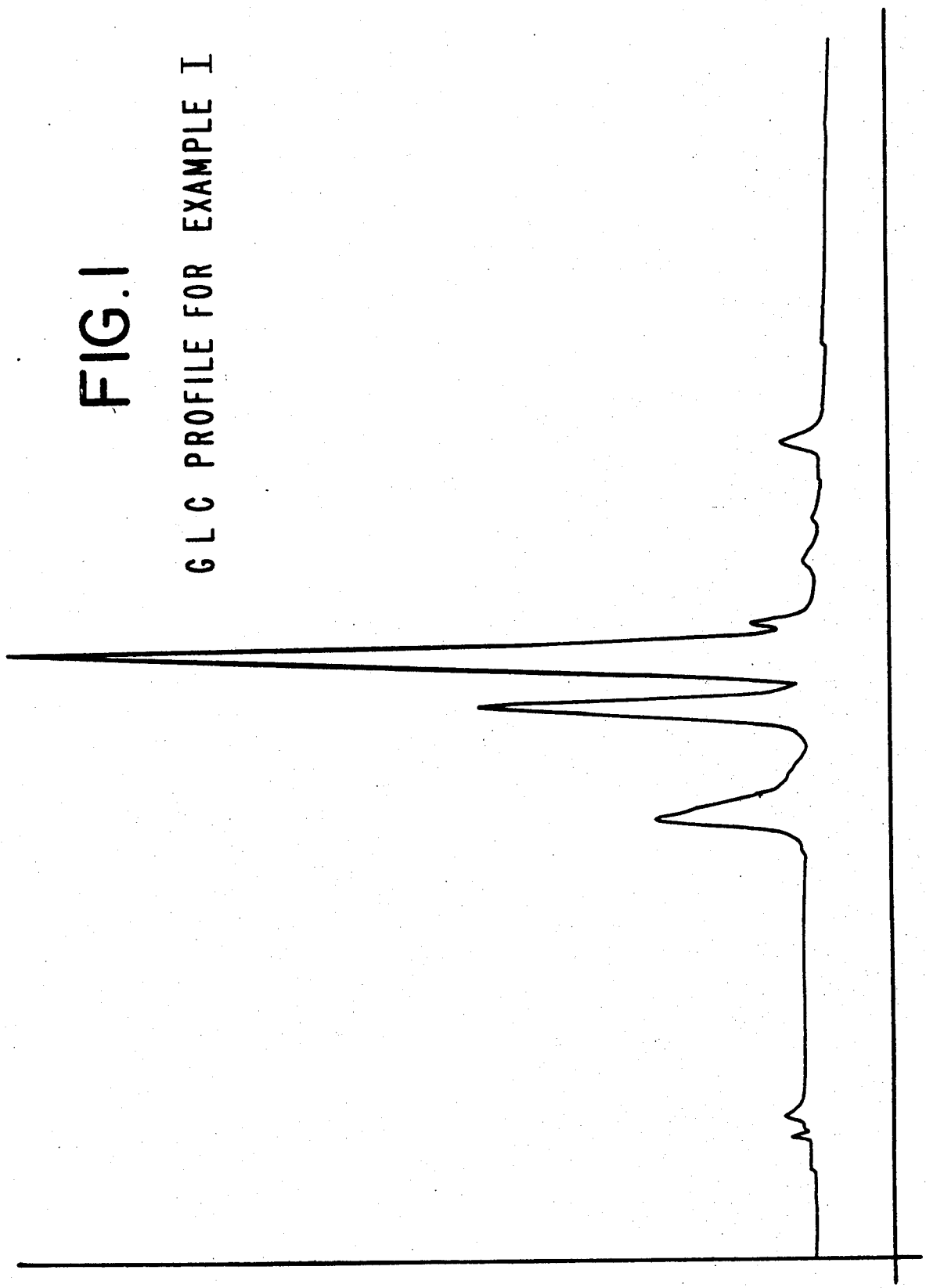
FIG. 1 is the GLC profile for the reaction product of Example I.
Figure 2:
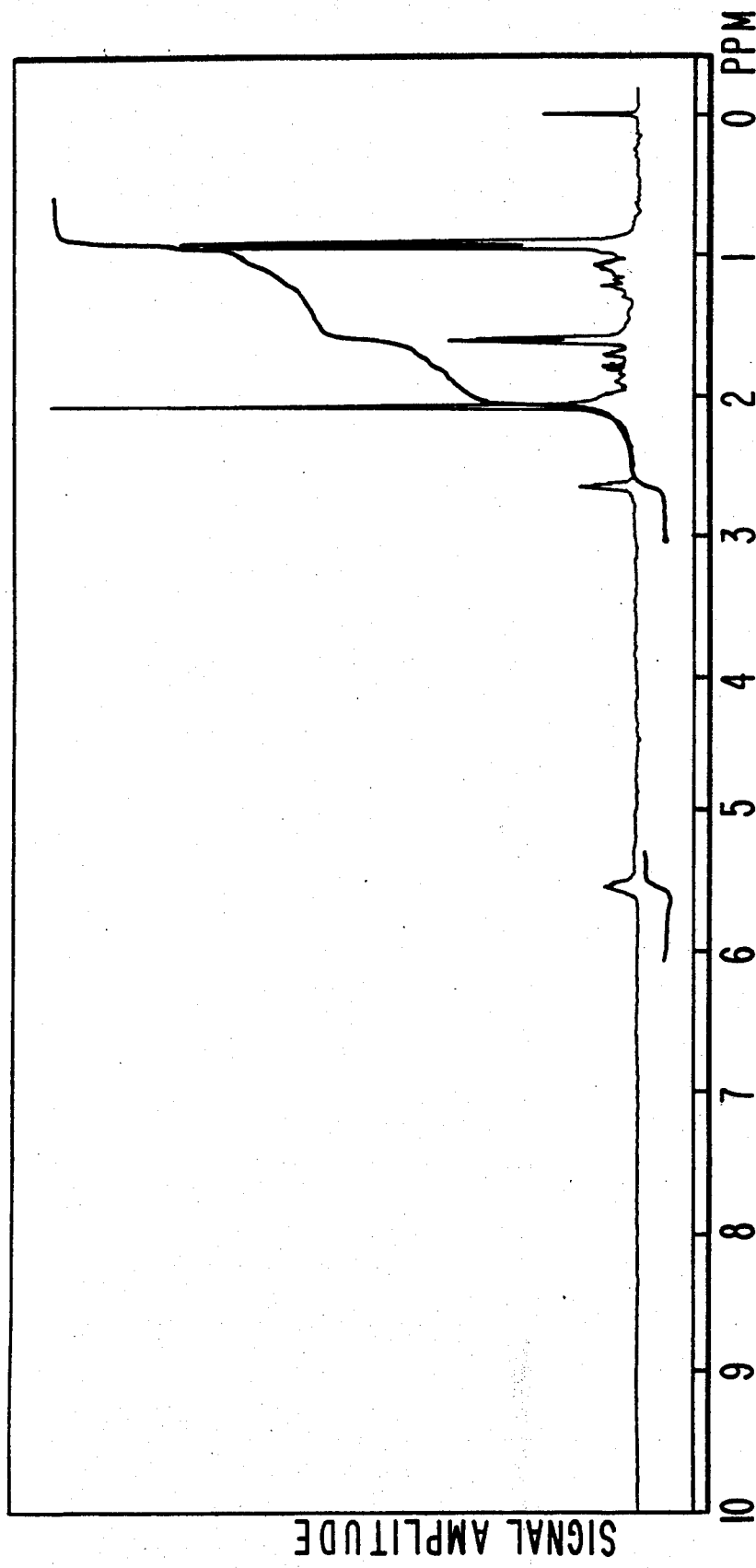
FIG. 2 is the NMR spectrum for peak 2 of Example I, peak 2 consisting essentially of compounds having the structures.

FIG. 1 is the GLC profile for the reaction product immediately after hydrogenation. FIG. 2 is the NMR spectrum for peak 2 of the GLC profile having the structure:

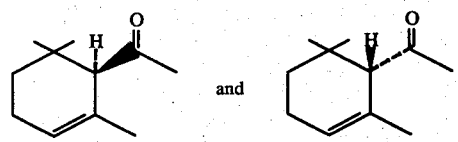

FIG. 3 is the NMR spectrum for peak 3 of the GLC profile consisting essentially of compounds having the structure:

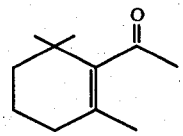

FIG. 4 is the infrared spectrum for peak 2 of the GLC profile having both structures:

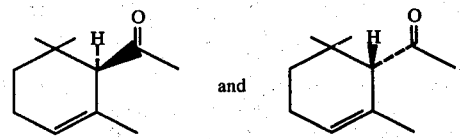

FIG. 5 is the infrared spectrum for peak 2 of the GLC profile consisting of compound having the structure:

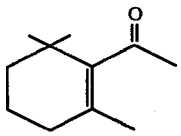

After adding 10 g Primol ® (a hydrocarbon mineral oil manufactured by the Exxon Corporation of Linden, New Jersey), the reaction product is distilled on a micro-Vigreux column yielding the following fractions:

| Fraction No. | Vapor Temp. | Liquid Temp. | Vac. mm. Hg. | Weight of Fraction (grams) |
| --- | --- | --- | --- | --- |
| 1 | 50/50 | 67/67 | 25/25 | 3.6 |
| 2 | 50 | 67 | 30 | 6.9 |
| 3 | 50 | 67 | 30 | 4.5 |

-continued

| Fraction No. | Vapor Temp. | Liquid Temp. | Vac. mm. Hg. | Weight of Fraction (grams) |
| --- | --- | --- | --- | --- |
| 4 | 50 | 67 | 30 | 8.4 |
| 5 | 50 | 67 | 30 | 11.8 |
| 6 | 50 | 75 | 30 | 9.3 |
| 7 | 50 | 90 | 30 | 3.8 |
| 8 | 45 | 190 | 30 | 1.2 |
|  |  |  |  | 49.5 |

EXAMPLE II

PREPARATION OF MIXTURE OF 1-(2',6',6'-TRIMETHYL-1'-CYCLOHEXYL)-3-HYDROXY-1-BUTANONE AND 1-(2',6',6'-TRIMETHYL-2-CYCLOHEXENYL)-3-HYDROXY-1-BUTANONE

Reactions:

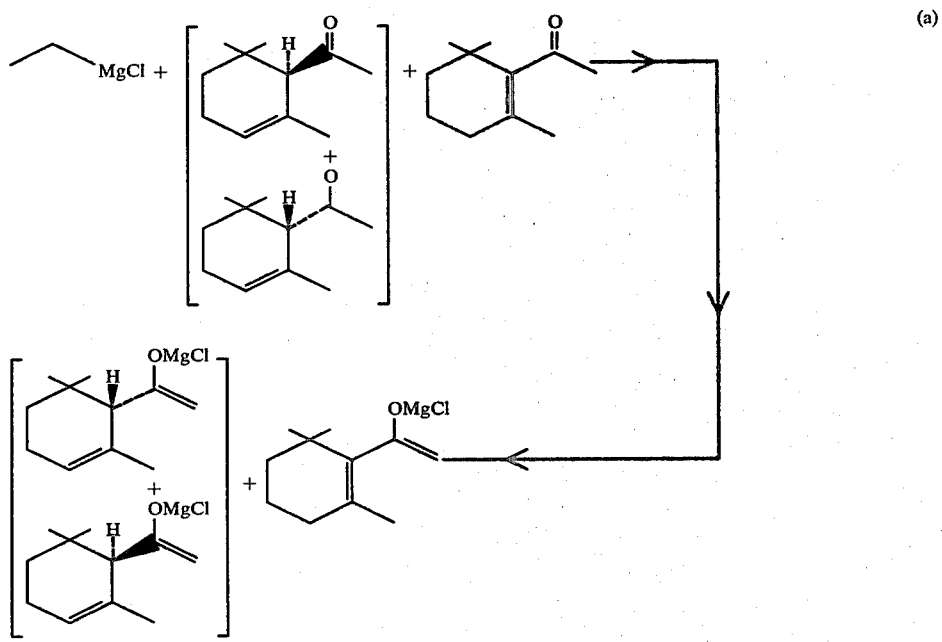

(a)

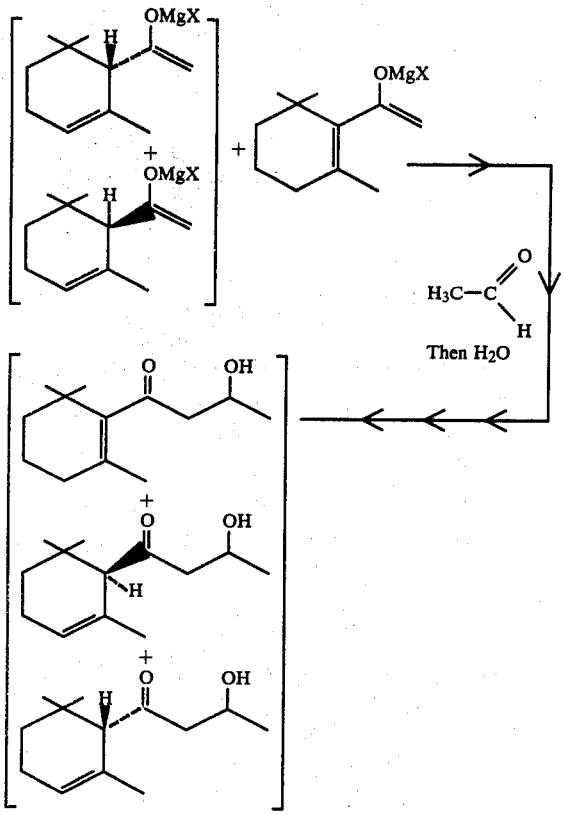

(b)

(wherein X is chloro).

Into a one liter reaction flask equipped with magnetic stirrer, thermometer, addition funnel, heating mantle, reflux condenser and nitrogen inlet tube are placed 120 ml ethyl magnesium chloride dissolved in tetrahydrofuran (concentration:3 molar). The contents of the reaction flask is heated to a temperature of 30°-35° C. Over a period of one hour, 40.4 grams of the 1-acetyl-2,6,6-trimethyl-cyclohex-1-ene prepared according to Example I (bulked fractions 1-7) is added to the ethyl magnesium chloride solution. The reaction mass is then stirred for an additional 30 minutes at 25°-35° C.

The reaction mass is then cooled to 0° C. and 12.0 grams of acetaldehyde dissolved in 40 ml of toluene is added over a one-hour period while maintaining the reaction mass at a temperature of 0°-10° C. The reaction mass is then stirred for an additional half hour at 0°-10° C.

144 grams of water is then added to the reaction mass and cooling is applied to maintain the temperature of the reaction mass at 15°-25° C. The addition of water is maintained over a period of 30 minutes.

The reaction product is then extracted with three volumes (50 ml each) of anhydrous diethyl ether. The reaction mass is then washed with four 75 ml volumes of saturated sodium chloride and the mass is dried over anhydrous magnesium sulfate. The solvent is then stripped off on a rotary evaporator yielding 49.8 grams of the product. After adding 3.0 grams Primol ®, the resulting product is then distilled on a three-inch microdistillation column yielding the following fractions:

| Fraction No. | Vapor Temp. | Liquid Temp. | Vac. mm. Hg. | Weight of Fraction (grams) |
|---|---|---|---|---|
| 1 | 40/77 | 78/91 | .056/.064 | .4 |
| 2 | 84 | 110 | .069 | 3.1 |
| 3 | 76 | 120 | .065 | .3 |
| 4 | 57 | 160 | .065 | .2 |
| | | | | 4.0 |

3 resulting from the distillation yield the date that the resulting product is a mixture of compounds having the structures:

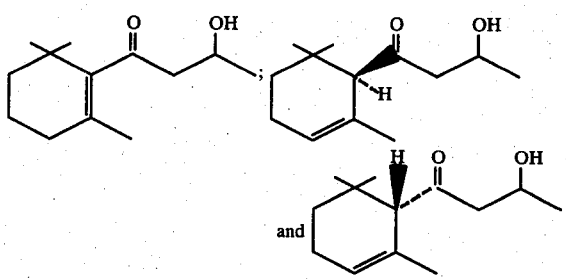

FIG. 8 is the infrared spectrum for the distillation fraction 3, which fraction contains the three compounds:

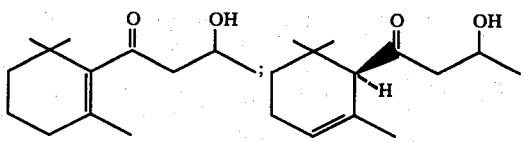

-continued

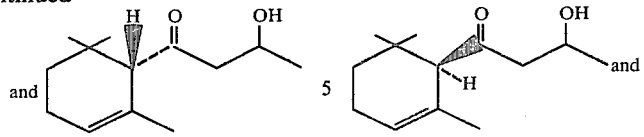

and

FIG. 9 is the NMR spectrum for distillation fraction 3 which contains the compounds having the structures:

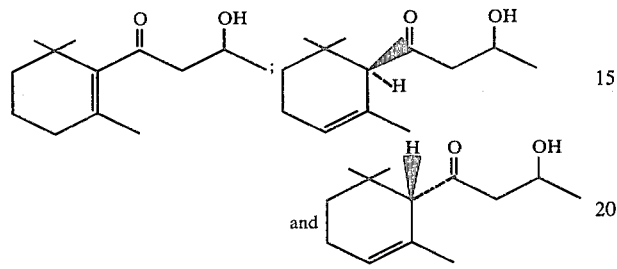

and

FIG. 6 is the mass spectrum for peak 2 of the GLC profile of distillation fraction 3 which peak consists essentially of compounds having the structure:

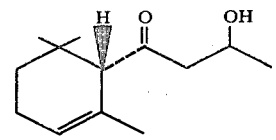

and

FIG. 7 is the mass spectrum for the compound of peak 3 of the GLC profile of distillation fraction 3 which peak consists essentially of compound having the structure:

EXAMPLE III

PREPARATION OF ALPHA DAMASCONE AND BETA DAMASCONE

Reaction:

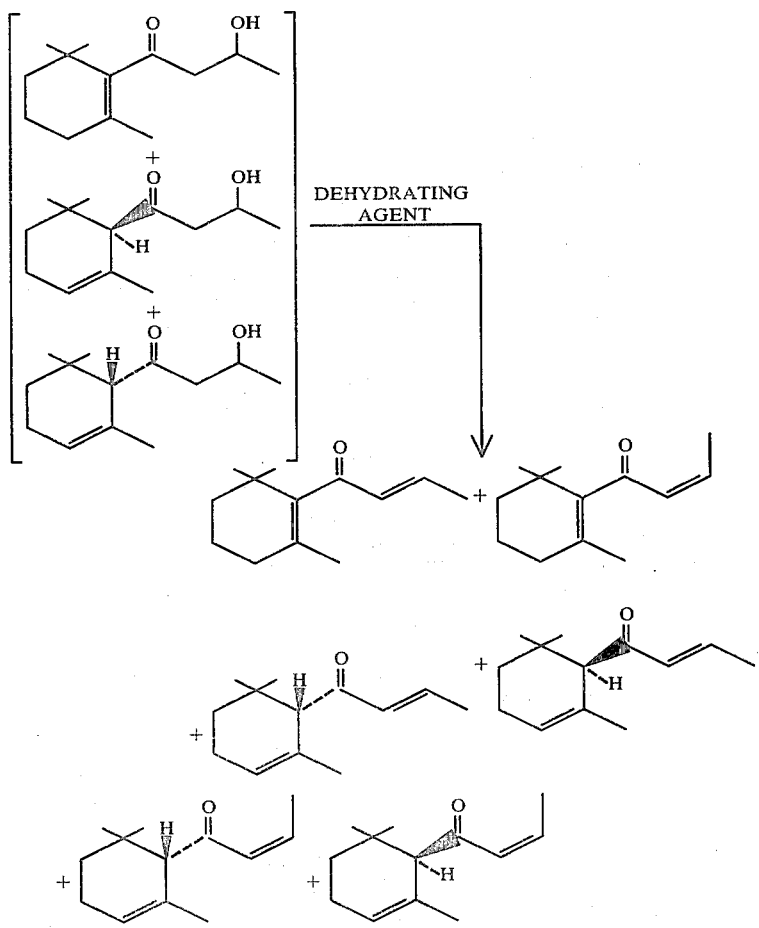

Into a 250 ml reaction flask equipped with magnetic stir, thermometer, addition funnel, reflux condenser and heating mantle is charged 2.0 grams of sodium acetate and 9.0 grams of acetic anhydride. The acetic anhydride/sodium acetate mixture is then heated to 105° C. The ketoalcohol mixture of Example II (44.8 grams in 25 ml toluene) consisting of compounds having the structures:

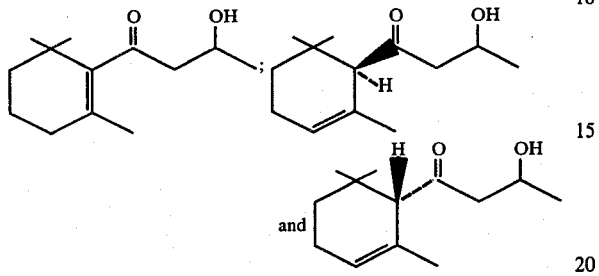

is added over a period of 1 hour while maintaining the temperature of reaction mass at 105°–110° C.

After the addition of the keto-alcohol mixture is complete, the reaction mass is heated at 110° C. for an additional 30 minutes. At the end of the 30-minute period, the reaction mass is cooled to 75° C. and approximately 150 grams of water is added. Cooling is required during the water addition to maintain the reaction mass at 75° C.

The reaction mass, now existing in two phases is separated and the aqueous phase is discarded. The resulting organic layer is washed with three 75 ml volumes of 10% sodium chloride (aqueous) and then three 50 ml volumes of water.

The solvent is then stripped from the reaction mass on a rotary evaporator and the crude material weighs 47.8 grams.

After adding 10.0 g Primol ®, the reaction mass is then distilled on an 8" rush-over column yielding the following fractions:

| Fraction No. | Vapor Temp. | Liquid Temp. | Vac. mm. Hg. | Weight of Fraction (grams) |
|---|---|---|---|---|
| 1 | 51/52 | 75/76 | .08/.08 | 1.1 |
| 2 | 54 | 79 | .08 | 1.1 |
| 3 | 59 | 82 | .08 | 1.4 |
| 4 | 60 | 84 | .08 | 3.0 |
| 5 | 62 | 86 | .08 | 3.6 |
| 6 | 65 | 89 | .08 | 4.1 |
| 7 | 68 | 92 | .08 | 4.1 |
| 8 | 73 | 97 | .08 | 3.2 |
| 9 | 80 | 111 | .10 | 4.3 |
| 10 | 103 | 142 | .10 | 4.0 |
| 11 | 110 | 200 | .10 | 3.7 |
| | | | | 33.6 |

NMR, IR and mass spectra data of the reaction product yield the information that the reaction product contains the following compounds:

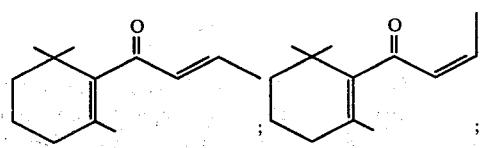

-continued

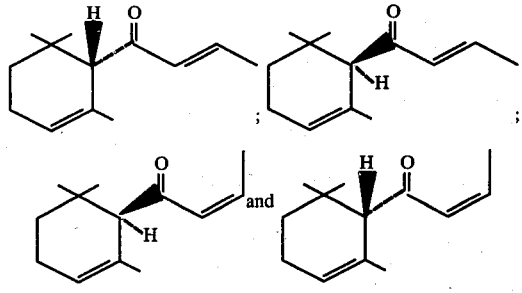

EXAMPLE IV

PERFUME COMPOSITION (ROSE FORMULATION)

The following rose perfume formulation is prepared:

| Ingredient | Parts by Weight |
|---|---|
| Rhodinol | 250 |
| Phenylethyl alcohol | 195 |
| Alpha methyl ionone | 80 |
| Linalyl acetate | 60 |
| Cis-3-hexenyl acetate | 5 |
| Jasmine absolute | 10 |
| Cinnamic alcohol | 20 |
| Rodinyl acetate | 60 |
| Cyclohexyl ethyl alcohol | 20 |
| Geraniol | 130 |
| Geranyl acetate | 80 |
| Paraisopropyl cyclohexanol | 60 |
| Diethyl phthalate | 30 |
| Mixture containing 30% of compounds having the structures: | |

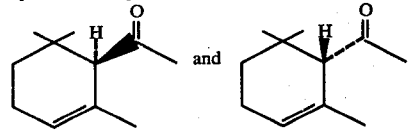

and 60% of compounds having the structure:

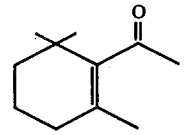

produced according to Example I

The mixture produced according to Example I imparts to this rose formulation a unique minty aroma with floral and hay-like undertones.

EXAMPLE V

PREPARATION OF SOAP CONTAINING PRODUCT OF EXAMPLE I

The mixture of 2,6,6-trimethyl-1-acetyl-cyclohexenes produced according to Example I is incorporated into soap (LVU-1) at rates of 0.1%, 0.2%, 0.3%, 0.4% and 0.5% by weight. After two weeks in the oven at 90° F., the resulting soaps show no visual effect from the heat. All soap samples have excellent minty-camphoraceous aromas with floral and hay-like undertones.

EXAMPLE VI

PERFUMED LIQUID DETERGENT

Concentrated liquid detergents with minty/camphoraceous aromas and floral, hay-like undertones (which detergents are produced from Lysine salt of n-dodecyl benzene sulfonic acid as more specifically described in U.S. Pat. No. 3,948,818, issued on Apr. 6, 1976) are prepared containing the mixture prepared according to Example I. They are prepared by adding and homogeneously mixing the appropriate quantity of 1-acetyl-2,6,6-trimethylcyclohexene mixture in the liquid detergent. The detergents all possess minty/camphoraceous aroma with floral, hay-like undertones, the intensity increasing with greater concentrations of the 1-acetyl-2,6,6-trimethylcyclohexene derivatives.

EXAMPLE VII

PREPARATION OF A DETERGENT COMPOSITION

A total of 100 grams of a detergent powder (a non-ionic detergent powder containing a proteolytic enzyme prepared according to Example I of Canadian Pat. No. 985,190 issued on Mar. 9, 1976) is mixed with 0.15 derivatives prepared according to Example I until a substantially homogeneous composition is obtained. This composition has an excellent minty/camphoraceous aroma with floral, hay-like undertones.

EXAMPLE VIII

PERFUMED LIQUID DETERGENTS

Concentrated liquid detergents with rich, pleasant, minty/camphoraceous aromas and floral, hay-like undertones are prepared containing 0.10%, 0.15% and 0.20% of the 1-acetyl-2,6,6-trimethylcyclohexene derivatives prepared according to Example I. They are prepared by adding and homogeneously admixing the appropriate quantity of 1-acetyl-2,6,6-trimethylcyclohexene derivatives prepared according to Example I in the liquid detergent. The liquid detergents are all produced using anionic detergents containing a 50:50 mixture of sodium lauroyl sarcosinate and potassium N-methyl lauroyl tauride. The detergents all possess a pleasant minty/camphoraceous aroma with floral, hay-like backgrounds, the intensity increasing with greater concentrations of the 1-acetyl-2,6,6-trimethylcyclohexene derivatives prepared according to Example I of this application.

EXAMPLE IX

TOBACCO FORMULATION

A tobacco mixture is prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of of the mixture produced according to Example I of 1-acetyl-2,6,6-trimethylcyclohexenes. The control cigarettes not containing the mixture of 1-acetyl-2,6,6-trimethylcyclohexenes produced according to the process of Example I and the experimental cigarettes which contain the mixture of 1-acetyl-2,6,6-trimethylcyclohexenes produced according to Example I are evaluated by paired comparison and the results are as follows:

The experimental cigarettes are found to have more body in tobacco smoke flavor and a fuller body sensation. The tobacco-like notes are described as "Virginia tobacco-like" and the flavor of the tobacco on smoking is sweeter and more aromatic. Prior to smoking, the flavor of the experimental cigarettes is described as musty-floral, slightly sweet, fruity and damascenone-like. All of the cigarettes are evaluated for smoke flavor with a 20 mm cellulose acetate filter.

EXAMPLE X

FLAVOR UTILITY OF 1-ACETYL-2,6,6-TRIMETHYLCYCLOHEXENES

The following lemon flavor formulation is prepared:

| Ingredients | Parts by Weight |
| --- | --- |
| Natural Lemon Oil, Terpeneless | 10 |
| Acetaldehyde | 0.6 |
| Alpha-terpineol | 2.1 |
| Citral | 1.8 |
| Carvone | 0.24 |
| Terpinolene | 1.2 |
| Alpha-terpinene | 0.25 |
| Diphenyl | 0.25 |
| Alpha Fenchyl Alcohol | 0.25 |
| Limonene | 0.35 |
| Linalool | 0.25 |
| Geranyl Acetate | 0.25 |
| Nootkatone | 0.25 |
| Neryl Acetate | 0.25 |

The flavor formulation is divided into two portions. Four parts per million of the mixture of 1-acetyl-2,6,6-trimethylcyclohexene derivatives produced according to Example II is added to 200 parts per million of the first portion of the lemon flavor prepared above; to the second portion of the lemon flavor nothing is added. A definite aroma improvement, a more natural lemon juice aroma and taste as well as a pleasant sour effect and generally improved taste is created as a result of the addition of the 1-acetyl-2,6,6-trimethylcyclohexene derivative mixture produced according to Example I to the lemon flavor. In general, the 1-acetyl-2,6,6-trimethylcyclohexene derivative mixture supplies a natural "lemon juice" note to this lemon flavor.

EXAMPLE XI

The mixture of 1-acetyl-2,6,6-trimethylcyclohexene derivatives prepared according to Example I is added at the rate of 10 ppm to Goya Guava Nectar (manufactured by Goya Manufacturing Co., New York, N.Y.). It is submitted to a bench panel which unanimously considers the guava nectar containing the 1-acetyl-2,6,6-trimethylcyclohexene derivative mixture produced according to Example I to have a fuller natural fresh guava character. The Goya Guava Nectar containing 1-acetyl-2,6,6-trimethylcyclohexene derivative mixture prepared according to Example I is preferred by the bench panel unanimously to the Goya Guava Nectar not containing said mixture of 1-acetyl-2,6,6-trimethylcyclohexene derivatives.

EXAMPLE XII

A. POWDER FLAVOR COMPOSITION

20 Grams of the flavor composition of Example X is emulsified in a solution containing 300 gm gum acacia and 70 gm water. The emulsion is spray-dried with a Bowen Lab Model Drier utilizing 260 c.f.m. of air with an inlet temperature of 500° F., an outlet temperature of 200° F., and a wheel speed of 50,000 rpm.

B. SUSTAINED RELEASE FLAVOR

The following mixture is prepared:

| Ingredients | Parts by Weight |
| --- | --- |
| Liquid Lemon Flavor Composition of Example X | 20 |
| Propylene glycol | 9 |
| Cab-O-Sil ® M-5 (Brand of Silica produced by the Cabot Corporation of 125 High Street, Boston, Mass. 02110; Physical Properties: Surface area: 200 m²/gm Nominal particle size: 0.012 microns Density: 2.3 lbs/cu.ft) | 5.00 |

The Cab-O-Sil is dispersed in the liquid lemon flavor composition of Example X with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XIII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example X is added to the solution which is then homogenized to form an emulsion having particle size typically in the range of 2–5 microns. This material is kept at 120° F. under which conditions the gelatin will not jell.

Coascervation is induced by adding, slowly and uniformly 40 parts by weight of a 20% aqueous solution of sodium sulphate. During coascervation the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XIV

CHEWING GUM

100 Parts by weight of chicle are mixed with 4 parts by weight of the flavor prepared in accordance with Example XII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE XV

CHEWING GUM

100 Parts by weight of chicle are mixed with 18 parts by weight of the flavor prepared in accordance with Example XII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE XVI

TOOTHPASTE FORMULATION

The following separate groups of ingredients are prepared:

| Parts by Weight | Ingredient |
| --- | --- |
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Luaroyl Sarcosinate (foaming agent) |
| Group "D" | |
| 1.200 | Flavor Material of Example XII |
| 100.00 (Total) | |

PROCEDURE:

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1–1.5 minutes).

EXAMPLE XVII

CHEWABLE VITAMIN TABLETS

The flavor material produced according to the process of Example XII is added to a Chewable Vitamin Tablet Formulation at a rate of 10 gm/Kg which chewable vitamin tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium mixture 1:1 | 70.00 |
| Vitamin B$_1$ (thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine Hydrochloride) as Rocoat ® pyridoxine hydrochloride 33⅓ | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XII | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant, long-lasting, consistently strong lemon flavor with a tropical fruit-like background for a period of 12 minutes.

EXAMPLE XVIII

The mixture of 1-acetyl-2,6,6-trimethylcyclohexenes produced according to Example I is added at the rate of 2% to a commercial peppermint oil (Cullison, Willanette, Redistilled USP). Peppermint oil with and without the 1-acetyl-2,6,6-trimethylcyclohexene produced according to Example I are compared at the rate of 10 ppm in water by a bench panel of experts. The product with the 1-acetyl-2,6,6-trimethylcyclohexene mixture has a more herbaceous, more peppermint, tea, slightly earthy note which is preferred by the bench panel.

What is claimed is:

1. A process for augmenting or enhancing the aroma of a perfume composition comprising the step of adding to a perfume composition an aroma augmenting or enhancing quantity of a mixture consisting essentially of compounds having the structures:

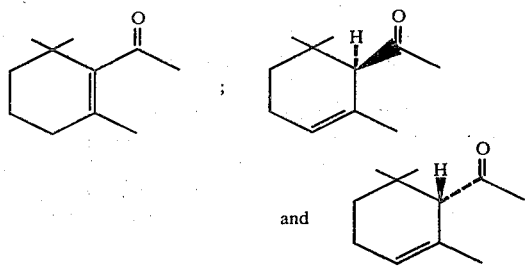

wherein the mixture contains 30% of the compounds having the structures:

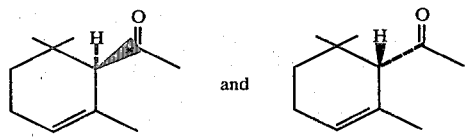

and 60% of the compound having the structure:

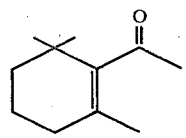

2. A perfume composition comprising a perfume carrier and a mixture consisting essentially of compounds having the structures:

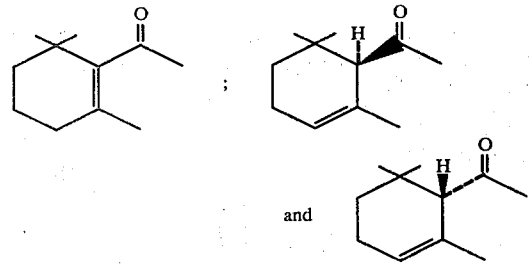

wherein the mixture contains 30% of the compounds having the structures:

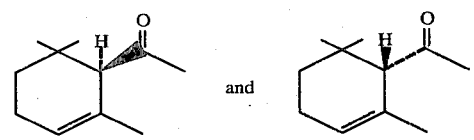

and 60% of the compound having the structure:

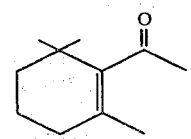

and add as an adjuvant therefor at least one alcohol, aldehyde or ketone other than any of the 1-acetyl-2,6,6-trimethylcyclohexene derivatives of said mixture, terpenic hydrocarbon, nitrile, ester, lactone, natural essential oil or synthetic essential oil.

3. A cologne comprising alcohol, water and an aroma augmenting or enhancing the quantity of a mixture consisting essentially of compounds having the structures:

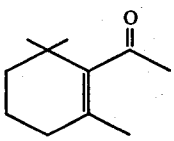 ; 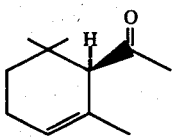

and 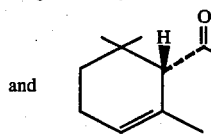

wherein the mixture contains 30% of the compounds having the structures:

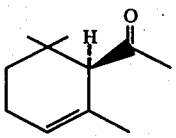 and 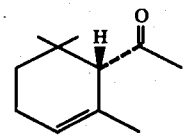

and 60% of the compound having the structure:

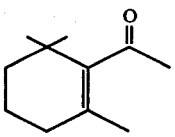

* * * * *